(12) United States Patent
Holländer

(10) Patent No.: US 9,422,542 B2
(45) Date of Patent: Aug. 23, 2016

(54) PROCESS FOR PARALLEL ISOLATION AND/OR PURIFICATION OF RNA AND DNA

(75) Inventor: Vera Holländer, Unna (DE)

(73) Assignee: Qiagen GmbH, Hilden (DE)

( * ) Notice: Subject to any disclaimer, the term of this patent is extended or adjusted under 35 U.S.C. 154(b) by 109 days.

(21) Appl. No.: 13/580,474

(22) PCT Filed: Feb. 25, 2011

(86) PCT No.: PCT/EP2011/000920
§ 371 (c)(1),
(2), (4) Date: Nov. 5, 2012

(87) PCT Pub. No.: WO2011/104027
PCT Pub. Date: Sep. 1, 2011

(65) Prior Publication Data
US 2013/0053254 A1    Feb. 28, 2013

(30) Foreign Application Priority Data

Feb. 26, 2010 (EP) .................................... 10001995
Mar. 3, 2010 (EP) .................................... 10002171

(51) Int. Cl.
*C07H 21/00* (2006.01)
*C12N 15/10* (2006.01)

(52) U.S. Cl.
CPC .................................. *C12N 15/1003* (2013.01)

(58) Field of Classification Search
CPC ...... C12N 15/1003; C12Q 1/68; C07H 21/04; B01D 11/02; B01D 17/02

USPC .............................................. 536/25.4, 25.41
See application file for complete search history.

(56) References Cited

U.S. PATENT DOCUMENTS

| | | | |
|---|---|---|---|
| 6,218,531 B1 | 4/2001 | Ekenberg | |
| 2005/0042660 A1 | 2/2005 | Hall, Jr. et al. | |
| 2007/0082354 A1 | 4/2007 | Leiser et al. | |
| 2009/0136971 A1* | 5/2009 | Krizman et al. | 435/7.92 |

FOREIGN PATENT DOCUMENTS

| | | |
|---|---|---|
| DE | 102005060738 A1 | 6/2007 |
| DE | 102008029356 A1 | 12/2009 |
| DE | 102008061714 A1 | 6/2010 |
| EP | 1 526 176 A2 | 4/2005 |
| EP | 1 767 361 A1 | 3/2007 |
| EP | 2 163 622 A1 | 3/2010 |
| WO | 01/46402 A1 | 6/2001 |

(Continued)

OTHER PUBLICATIONS

RNeasy FFPE Handbook, Qiagen, Jan. 2006, 28 pages.*

(Continued)

*Primary Examiner* — Jezia Riley
(74) *Attorney, Agent, or Firm* — Seed IP Law Group PLLC

(57) ABSTRACT

The present invention relates to a process for the parallel isolation and/or purification of RNA and DNA from the same fixed biological sample, the quantification and analysis of the nucleic acids isolated by the process according to the invention, to a kit for the parallel isolation and/or purification of RNA and DNA from a fixed sample and to the use of this kit for the diagnosis, prognosis, decision with respect to therapy and/or the monitoring of the therapy of a disease.

55 Claims, 4 Drawing Sheets

(56) References Cited

FOREIGN PATENT DOCUMENTS

| WO | 03/064605 A2 | 8/2003 |
|---|---|---|
| WO | 2005/012523 A1 | 2/2005 |
| WO | 2005/054466 A2 | 6/2005 |
| WO | 2005/075642 A1 | 8/2005 |
| WO | WO 2006083962 A1 * | 8/2006 |
| WO | 2007/068764 A1 | 6/2007 |
| WO | 2008/021419 A2 | 2/2008 |
| WO | 2009/144182 A1 | 12/2009 |

OTHER PUBLICATIONS

Protein Purification Extraction and Clarification. European Molecular Biology Laboratory, Feb. 1, 2002. [online] [retrieved on Jul. 25, 2013]. Retrieved from the Internet: <http://www.embl.de/pepcore/pepcore_services/protein_purification/extraction_clarification/lysis_buffer_additives/>.*
Kristensen, L. et al 2009 BMC Cancer 9: 453.*
Tucker et al 2009 American Journal of Human Genetics 85: 142-154.*
Tan et al Feb. 2006 Biophysical Journal 90: 1175-1190.*
International Search Report and Written Opinion, mailed May 27, 2011, for PCT/EP2011/000920, 10 pages.
International Search Report and Written Opinion, mailed May 27, 2011, for PCT/EP2011/000930, 9 pages.
Genov et al., "Stability of subtilisins and related proteinases (subtilases)," *Int J Peptide Protein Res* 45:391-400, 1995.
miRNeasy FFPE Handbook, QIAGEN, Sep. 2010, 41 pages.
O'Shea et al., "Analysis of T receptor β chain CDR3 size using RNA extracted from formalin fixed paraffin wax embedded tissue," *J Clin Pathol* 50:811-814, 1997.
RNeasy FFPE Handbook, QIAGEN, Sep. 2010, 41 pages.

* cited by examiner

Figures

P: Sample, K: Control, M: Marker Lambda/HindIII

PROCESS FOR PARALLEL ISOLATION AND/OR PURIFICATION OF RNA AND DNA

The present invention relates to a process for the parallel isolation and/or purification of RNA and DNA from the same fixed biological sample, the quantification and analysis of the nucleic acids isolated by the process according to the invention, a kit for the parallel isolation and/or purification of RNA and DNA from a fixed sample and the use of this kit for the diagnosis, prognosis, decisions with respect to therapy and/or the monitoring of the therapy of a disease.

If biological material, such as, for example, a tissue fragment or isolated cells, is removed from a living organism, the cells die within a short period of time. Very rapidly, the dead cells are broken down first by autolysis/fermentation and then bacterially, so that the original cell and tissue structures are destroyed. If cells or tissue fragments are to be removed from an organism for histological examination, it is therefore recommended to fix the biological sample taken to prevent degradation. Ideally, fixation leaves the structures of the sample substantially unchanged to allow histological assessment thereof. Fixation furthermore allows long-term preservation and archiving of the samples. For these reasons, many morphological examinations are only possible based on fixed material.

Usually, fixation is achieved using protein-precipitating or protein-crosslinking compounds such as, for example, acids, alcohols, ketones or aldehydes, in particular glutaraldehyde or formaldehyde. Here, fixation with formaldehyde (employed in the form of an aqueous solution referred to as "formalin") followed by embedding of the fixed sample in paraffin is of major importance especially in pathology since cell and tissue structures are preserved particularly well. Hereinbelow, material fixed in this manner is referred to as "formalin-fixed, paraffin-embedded material" or "FFPE material".

However, fixation of a sample, in particular with formalin, has the disadvantage that, owing to the crosslinking effect of the formaldehyde, not only proteins but also various other biomolecules including the nucleic acids present in the sample are covalently attached to one another, and as a consequence the isolation of the nucleic acids (DNA or RNA) from such samples is very difficult. For numerous investigations on a molecular level, however, isolation of the nucleic acids is of great importance.

One way of isolating nucleic acids from such fixed samples is described in WO 2007/068764. The method described therein makes it possible to break the crosslinks formed by fixation in the biological sample and to isolate one type of nucleic acid, that is either DNA or RNA, which may then be followed, for example, by PCR or RT-PCR analysis.

In the field of molecular pathology, for example for the diagnosis or prognosis of tumour disorders, both DNA-based and RNA-based analysis are employed. To allow both DNA- and RNA-based analyses on the same fixed samples, for example tumour samples, a process is required which permits parallel isolation of DNA and RNA from one sample, such as, for example, a tissue section from a biopsy. Such a parallel isolation of DNA and RNA from a single sample is highly desirable, since, firstly, there is usually available only a very small amount of sample material which is insufficient for a plurality of separate purifications. Secondly, the composition of the sample material is, in general, heterogeneous; for example, only very few tumour cells are present in a matrix of healthy cells. In this case, it is not desirable to split the sample as it is impossible to ensure that the ratio of the different cells to one another is the same in each partial sample. Only the parallel isolation of DNA and RNA from a single undivided sample ensures that all analytes to be studied are present in the same ratio and originate from a sample of identical composition.

The process described in WO 2007/068764 releases both types of nucleic acid, DNA and RNA, equally by breaking the crosslinks introduced during fixation. This process therefore only permits the isolation either of DNA or RNA or else of a mixture of both nucleic acids; it does not, however, allow parallel isolation of DNA and RNA in separate fractions. To separate the two types of nucleic acid (DNA and RNA), WO 2007/068764 suggests, after isolation, selective precipitation or selective adsorption of one of the two types of nucleic acid released simultaneously during purification. Alternatively, it is possible to degrade the respective unwanted type of nucleic acid enzymatically.

One method for the parallel purification of DNA and RNA from a sample by selective adsorption is known and can be carried out, for example, using the commercially available Allprep DNA/RNA Kit (Qiagen, Hilden, Germany). Here, the sample is initially lysed in a chaotrope-containing lysis buffer without any alcohol, and the DNA present in the lysate is bound to a silica matrix, whereas the RNA also present in the lysate remains unattached in solution. After addition of an alcohol to the remaining lysate the RNA can be attached to a further silica matrix. This process works well for non-fixed samples. However, it has been found that it is still not optimally applicable to formalin-fixed samples since here the DNA does not bind quantitatively to the first silica matrix, but large amounts remain in the residual lysate and are purified together with the RNA. Therefore, this process does not allow separate purification of RNA and DNA.

WO2005/075642 describes a method for simultaneous extraction of DNA and RNA from a biological sample, including FFPE samples. The FFPE sample is deparaffinised and digested using a lysis buffer comprising a chaotropic agent, an ionic detergent and a proteolytic enzyme. The sample is digested for at least 5, preferably 10 hours to release the RNA and DNA, phenol-chloroform is added and the phases are separated. The aqueous phase comprises mainly RNA, the organic phase mainly DNA. RNA can then be recovered from the aqueous phase using alcohol precipitation. The DNA is recovered from the organic phase. This method has inter alia the drawback that it requires the extraction of the released nucleic acids using phenol in order to be able to separate the RNA from the DNA prior to isolating said nucleic acids separately from the organic and the aqueous phase.

A similar protocol is described in O'Shea et al, "Analysis of T cell receptor beta chain CDR3 size using RNA extracted from formalin fixed paraffin wax embedded tissue" J Clin Pathol 1997; 50:811-814.

Commercially available kits for isolating mixtures of DNA and RNA or either DNA or RNA from FFPE samples are likewise known. The FFPE RNA/DNA Purification Kit (Norgen, Biotek Corp., Thorold, Canada) allows the isolation of a mixture of RNA and DNA in one eluate. Here, to obtain either only DNA or only RNA, a particularly long protease K digestion and a RNAse treatment may be carried out to isolate the DNA or a short protease K digestion and a DNAse treatment may be carried out to isolate the RNA. However, this kit does not allow simultaneous but separate purification of both types of nucleic acid from the same sample.

The Agencourt FormaPure Kit (Beckman Coulter Genomics GmbH, Danvers, Mass., USA), too, allows the isolation of a mixture of RNA and DNA in one eluate or the isolation of RNA after DNAse digestion, but not simultaneous but separate isolation of RNA and DNA.

The option to obtain either DNA or RNA by corresponding nuclease digestion or by a suitable heat incubation is also provided by the Ambion Recover All FFPE Kit (Applied Biosystems, Inc., Foster City, Calif., USA) and the QuickExtract FFPE RNA Extraction Kit (Epicentre Biotechnologies, Madison, Wis., USA). However, none of these commercially available kits allows the separate purification of both DNA and RNA from the same fixed sample.

Furthermore, WO 2005/075642 describes a process for the simultaneous extraction of both types of nucleic acids (RNA and DNA) from the same sample, which may also be a fixed sample, inter alia. This process comprises, after lysis of the sample and enzyme deaktivation using aromatic alcohols, a separation of the two types of nucleic acid by a suitable extraction process. However, from the two phases obtained in this process (an aqueous phase comprising RNA, and an organic phase comprising DNA), the nucleic acids then have to be precipitated by addition of suitable precipitating agents prior to further purification and/or isolation. Firstly, this renders the process time-consuming, and secondly, because of the precipitation, there is a risk of substance losses and/or of the nucleic acids being contaminated by the precipitating agent.

Accordingly, it was an object of the present invention to provide a process allowing separate purification of both DNA and RNA from the same sample fixed by crosslinking, the separation of DNA from RNA requiring neither organic solvents nor solid matrices for bindung the nucleic acids.

SUMMARY OF THE INVENTION

The present invention is inter alia based on the finding that the partial proteolysis of the protein-containing components of a biological sample fixed by cross-linking using at least one proteolytically active compound allows to selectively release the RNA into a dissolved fraction of the sample, while the DNA predominantly remains in the undissolved residue of said sample. Said partial digestion of the sample allows to obtain separate fractions, wherein the dissolved fraction comprises mainly RNA and the undissolved residue comprises mainly DNA. The mainly RNA containing dissolved fraction can be easily separated from the mainly DNA containing undissolved residue e.g. using a centrifugation process.

After separation of the dissolved from the undissolved fraction, the fractions can be separately processed as desired. E.g. the RNA can be isolated from the undissolved fraction and the DNA can be isolated from the undissolved fraction. The separation of the mainly RNA containing dissolved fraction from the mainly DNA containing undissolved fraction prior to isolating the nucleic acids from the individual fractions allows to efficiently isolate RNA and DNA from the same cross-linked sample with good yield. It is also within the scope of the present invention to isolate the nucleic acid only from one fraction and discard the other fraction. E.g. if the isolation of RNA is in focus, the DNA containing undissolved fraction can be discarded after separation.

Other objects, features, advantages and aspects of the present application will become apparent to those skilled in the art from the following description and appended claims. It should be understood, however, that the following description, appended claims, and specific examples, while indicating preferred embodiments of the application, are given by way of illustration only. Various changes and modifications within the spirit and scope of the disclosed invention will become readily apparent to those skilled in the art from reading the following.

DETAILED DESCRIPTION OF THE INVENTION

As discussed above it was one object of the present invention to provide a process allowing separate purification of both DNA and RNA from the same sample fixed by crosslinking, the separation of DNA from RNA requiring neither organic solvents nor solid matrices for bindung the nucleic acids.

This object is achieved by a process for the parallel isolation and/or purification of ribonucleic acids (RNA) and deoxyribonucleic acids (DNA) from the same biological sample fixed by crosslinking, comprising the following steps:
   a) partial dissolution of the sample in an aqueous buffer solution with simultaneous partial proteolysis of the protein-containing components of the sample using at least one proteolytically active compound to obtain a dissolved fraction (fraction A) and an undissolved residue (pellet; fraction B),
   b) separation of the dissolved fraction from the undissolved residue,
where the dissolved fraction comprises mainly RNA, based on the total amount of nucleic acids in the dissolved fraction, and the undissolved residue comprises mainly DNA, based on the total amount of nucleic acids in the undissolved residue,
and where the separation of the fraction comprising predominantly RNA from the fraction comprising predominantly DNA requires neither precipitation nor extraction of one or both types of nucleic acid with organic solvents nor selective binding of one or both types of nucleic acid to a solid matrix.

For the purpose of the process according to the invention, parallel isolation and/or purification is understood as meaning an isolation and/or purification where the isolation and/or purification of the two types of nucleic acid, RNA and DNA, takes place spatially separated from one another, where the treatment of the two fractions A and B, one of which comprises predominantly RNA and the other of which comprises predominantly DNA, can occur simultaneously or else at different points in time.

For the purpose of the invention, the same biological sample fixed by crosslinking is understood as meaning the entire sample subjected to the partial lysis in step a).

For the purpose of the invention, the terms "partial dissolution" and "partial proteolysis" or "partial digestion" are understood as meaning the partial dissolution of the sample or individual components of the sample and the partial degradation of the protein-containing components of the sample, respectively, as illustrated in more detail below.

For the purpose of the invention, if a fraction is referred to as comprising predominantly one type of nucleic acid, it comprises more than 50% by weight of this type of nucleic acid, based on the total amount of nucleic acids (i.e. the sum of the two types of nucleic acid) in this fraction. According to one embodiment, said fraction comprising predominantly one type of nucleic acid comprises at least 60%, preferably at least 70%, more preferred at least 80% by weight of this type of nucleic acid, based on the total amount of nucleic acids in this fraction.

The process according to the invention allows the parallel isolation of DNA and RNA from the same fixed sample in separate fractions and their subsequent analysis by sensitive, qualitative and/or quantitative methods, where even small amounts of sample as obtained, for example, from microscopically analyzable sections of clinical biopsies with hollow needles of a diameter of a few mm, are suitable as sample material. In the process according to the invention, in contrast to the commercially available Allprep DNA/RNA Kit (Qiagen, Hilden, Germany), the separation into a DNA-comprising and an RNA-comprising fraction takes place before the actual purification of the nucleic acids. From the fixed biological sample, the process according to the invention generates two fractions, the dissolved fraction comprising predominantly RNA and the undissolved fraction comprising predominantly DNA. In a further step, these fractions can be utilized for further extraction and/or purification of the respective nucleic acid. The partial digestion and subsequent separation of the RNA from the DNA into a mainly RNA containing dissolved fraction and a mainly DNA containing undissolved fraction also differentiates the method according to the present invention from prior art methods that are based on a phenol/chloroform extraction for separating the DNA from the RNA. In respective phenol/chloroform based methods, DNA and RNA are both released into the lysate and accordingly, are both present in the dissolved fraction. After phenol-chloroform extraction and phase separation, the RNA is dissolved in the aqueous phase and the DNA is present in a dissolved form in the organic phase. Thus, the prior art separation principle fundamentally differs from the process according to the present invention which does not require a phenol/chloroform extraction for separating the RNA from the DNA but inter alia relies on a partial digestion of the cross-linked sample to keep the DNA predominantly in the undissolved fraction while the RNA is released into the dissolved fraction.

In a first step, the FFPE sample is preferably subjected to a protease treatment. Surprisingly, it has been found that, by optimization of adjusting the conditions of this proteolysis (the enzymatic "digestion") of the proteins by using a protease in this first protease treatment, it is possible to release selectively only the RNA, but not the DNA, from the sample. Using a suitable separation process, for example centrifugation, it is possible to separate, after the incomplete "digestion" according to the invention of the sample, a still undissolved fraction comprising DNA from the RNA-comprising supernatant.

Here, the separation of the two fractions into a dissolved fraction (A) and an undissolved fraction (B) can be carried out using any method known to the person skilled in the art as being suitable for separating liquid and solid components, such as, for example, filtration, sedimentation, decantation, centrifugation, etc. Hereinbelow, the undissolved residue obtained in this step is also referred to as pellet, where, for the purpose of the invention, this term is explicitly not limited to an undissolved residue separated off from the liquid component of the sample by centrifugation, but also includes undissolved residues separated off by other means, for example the solid material that remains on the filter after a filtration.

Pelleting the undissolved fraction is advantageous because it allows the easy and efficient separation of the two fractions.

For isolating the RNA, the RNA-comprising supernatant can be treated by a customary process known from the state of the art, for example by the process described in the application WO 2007/068764, which comprises heat incubation in a nucleophile-comprising solution to remove remaining crosslinks, where the RNA can then be isolated, for example, by binding to a silica matrix using, for example, the RNeasy FFPE Kit (QIAGEN, Hilden, Germany).

The undissolved fraction, which comprises the DNA and other undissolved components of the incompletely digested sample, is used for isolating the DNA. Here, it is possible to use any methods suitable or according to the state of the art customary for isolating DNA from fixed samples, since the pellet still has essentially the properties of a fixed sample. In particular, the preceding incomplete protease digestion has not removed any substantial amounts of DNA from the sample and/or has not removed DNA crosslinks in any significant amount. To this end, another or an additional enzymatic protease digestion is advantageously carried out to lyse the sample completely, followed by heat incubation in a nucleophile-containing solution such as described, for example, in WO 2007/068764. The DNA released in this manner can then be purified further with the aid of any suitable method, for example by binding to a silica matrix using, for example, the QIAamp FFPE Kit (QIAGEN).

In this manner, both types of nucleic acid are pre-fractionated from a single sample in one step and then isolated separately from one another and thus made available to further analysis methods.

For the purpose of the invention, the term nucleic acids includes all nucleic acids known to the person skilled in the art, for example natural or synthetic nucleic acids, and also nucleic acids artificially introduced into the sample, single- and double-stranded nucleic acids, straight-chain, branched or circular nucleic acids, RNA, in particular mRNA, siRNA, miRNA, snRNA, tRNA, hnRNA or ribozyms, DNA, in particular genomic or plastidic DNA or DNA from organelles, and also nucleic acids of infectious origin.

Suitable biological samples are all biological samples suitable for fixation, such as, for example, cell-containing bodily fluids such as blood, sperm, cerebrospinal fluid, saliva, sputum or urine, leukocyte fractions, buffy coats, faeces, surface biopsies, aspirates, skin fragments, entire organisms, organs and tissue of Metazoa, preferably of insects and mammals, in particular of humans, for example in the form of autopsies, biopsies, fine-needle aspirates or tissue sections, isolated cells, for example in the form of adherent or suspended cell cultures, plants, parts of plants, plant tissue or plant cells, bacteria, viruses, yeast and fungi.

In a first step a) of the process according to the invention, the fixed sample is brought into contact with a preferably aqueous solution which permits the activity of a proteolytically active compound, and also with one or more proteolytically active compounds.

For the purpose of the invention, proteolytically active compounds are all protein-cleaving compounds, preferably proteolytically active enzymes such as proteases and heat-stable proteases, particularly preferably proteinase K, trypsin, chymotrypsin, papain, pepsin, pronase and endoproteinase Lys-C, in particular proteinase K and also non-enzymatic substances suitable for cleaving proteins, such as cyanogen bromide, or mixtures of these substances.

The concentration of the proteolytically active compound in the aqueous solution generally depends on the nature of the proteolytically active compound and on the nature and the amount of the biological sample and can be determined by the person skilled in the art using simple routine experiments. The concentration of a protease enzyme in the aqueous solution is preferably in a range of from 0.001 to 5% by weight, particularly preferably 0.01-2.5% by weight and in particular 0.05-0.2% by weight, in each case based on the total weight of the aqueous solution. Here, the amount or the concentration of the proteolytically active compound to be used for a certain sample depends on the nature of the proteolytically active compound and the chosen reaction conditions, such as pH, cofactors, incubation temperature and incubation time, something the person skilled in the art is familiar with. The suitable amount or concentration of the proteolytically active compound can be determined in a simple manner by routine experiments. It has furthermore been found that in the process according to the invention it is in any case not critical that the amount or concentration of the proteolytically active compound is specifically adjusted, but that it may be varied over a certain band width without negatively affecting the yield of nucleic acid or its integrity (Example 2).

The aqueous solution preferably contains further substances which promote the degradation of the biological tissue and/or the lysis of cells, such as, for example, chaotropic reagents and/or, preferably, surfactants.

Surfactants suitable for use in the process according to the invention are all surfactants known to the person skilled in the art and suitable for lysing cells; preference is given here to anionic or nonionic surfactants. Preferred surfactants are compounds selected from the group comprising sodium dodecylsulphate (SDS), sodium deoxycholate, 3-(3-cholamidopropyl)dimethylammonium-1-propanesulphonate (CHAPS), polyethylene glycol phenyl ethers, such as, for example, the surfactants available under the trade names Triton X-100, Tween or NP-40 or mixtures of these, preferred surfactants being SDS, NP-40 and Triton X-100 (polyethylene glycol (1,1,3,3-tetramethylbutyl)phenyl ether having a degree of ethoxylation of from 9 to 10). The amount of surfactant employed for supporting the lysis of the cells present in the biological sample depends on the nature and the amount of the biological sample and can be determined by the person skilled in the art using simple routine experiments.

The aqueous solution is furthermore preferably a buffer solution, the pH of which is stabilized by at least one buffer substance present in the solution to a range of from 6 to 9, preferably from 6.5 to 8.5 and particularly preferably from 6.8 to 7.5. Accordingly, the aqueous buffer solution preferably comprises at least one buffer substance, preferably selected from the group comprising Tris, Hepes, Pipes, Mops, alkali metal acetate/acetic acid etc. and/or preferably at least one surfactant, preferably selected from the group comprising sodium dodecylsulphate (SDS), sodium deoxycholate, 3-(3-cholamidopropyl)dimethylammonium-1-propanesulphonate (CHAPS), polyethylene glycol phenyl ethers or mixtures of these, particularly preferably sodium dodecylsulphate, polyethylene glycol nonylphenyl ether having a degree of ethoxylation of 40, obtainable under the trade name Tergitol-type NP-40, and/or polyethylene glycol (1,1,3,3-tetramethylbutyl)phenyl ether having a degree of ethoxylation of 9-10.

The aqueous solution may furthermore comprise additional components which support the lysis, protect the nucleic acids against decomposition constituents and/or stabilize the aqueous solution, for example complexing agents, reducing agents or other buffer substances, where the person skilled in the art is familiar with the nature and amount of possible additives for lysis buffers or is able to determine them by simple routine experiments. In a preferred embodiment, the aqueous buffer solution furthermore comprises at least one substance selected from the group comprising complexing agents, preferably ethylenediamine-N,N,N', N'-tetraacetic acid (EDTA), ethylene glycol bis(2-aminoethyl ether)-N,N,N',N'-tetraacetic acid (EGTA) sodium citrate or mixtures of these, chaotropic agents, preferably selected from the group comprising guanidine hydrochloride, guanidine thiocyanate, guanidine isothiocyanate, perchlorates, NaI, KI and urea, preferably in a concentration of from 0.1 to 10 M, reducing agents, preferably selected from the group comprising dithiothreitol (DTT), dithioerythritol (DTE), sodium thiosulphate, β-mercaptoethanol or mixtures of these, and inorganic salts, preferably alkali metal halides, such as, for example, NaCl, KCl or LiCl, alkaline earth metal halides, such as, for example, $CaCl_2$ or $MgCl_2$, ammonium salts, such as, for example, ammonium chloride or ammonium sulphate, lithium sulphate or mixtures of these.

According to one embodiment, the aqueous buffer solution comprises a detergent, preferably a non-ionic detergent such as SDS, and preferably a buffering agent, preferably TRIS. The aqueous buffer solution may also comprise a chelating agent such as EDTA.

In process step a) of the process according to the invention, the biological sample fixed by crosslinking is brought into contact with the aqueous solution comprising at least one proteolytically active compound and incubated at a suitable temperature. Here, the temperature generally depends on the nature of the proteolytically active compound employed. In the case of enzymes, a temperature has to be chosen which permits the enzyme to be active. In general, temperatures which are too low reduce the enzyme activity up to the point of inactivity, whereas temperatures which are too high may deactivate the enzyme by denaturation. The temperature range tolerated by the enzyme in question or the optimum reaction temperature vanes depending on the respective enzyme and is known to the person skilled in the art or can be determined by simple routine experiments. When using proteinase K, for example, the reaction can be carried out at temperatures of up to about 95° C., preferably between 18° C. and 80° C., particularly preferably between 50 and 65° C.

As already described, it has surprisingly been found that, by optimization of the adjustment of the conditions of the proteolytic "digestion" of the proteins in a fixed sample using a proteolytically active compound, preferably a protease, it is possible to remove selectively only the RNA, but not the DNA, from the sample. After this incomplete (partial) digestion according to the invention of the sample, a still undissolved fraction comprising the DNA may be separated from the RNA-comprising dissolved supernatant. For a given proteolytically active compound, the quality of the separation into RNA and DNA depends on their concentration and the incubation temperature and in particular on the incubation time. If the proteolytically active compound is allowed to react only for a very short time, not only the DNA but also the RNA are detached only insufficiently from the sample and therefore in total only a low yield of nucleic acid in the soluble fraction is obtained. In contrast, if the proteolytically active compound is allowed to react for too long, the result will be (almost) complete dissolution of the RNA, but also more DNA detached from the pellet.

However, by properly adjusting the reaction time of the proteolytically active compound, it is possible to achieve partial (incomplete) lysis of the sample with substantial separation between RNA in the soluble fraction and DNA in the undissolved fraction, that is a "prefractionation" of the two types of nucleic acid prior to the actual purification.

Here, the optimal reaction time depends firstly on the proteolytically active compound, its concentration in the aqueous solution and the incubation temperature. Secondly, the amount and thickness of the biological sample and other sample-specific parameters, for example the type and the duration of the fixation have an effect on the optimum reaction time of the proteolytically active compound.

Preference is given to using samples fixed with formalin, in particular after the sample has been embedded in paraffin. For relatively large tissue blocks, because of the large quantity and thickness of the sample, a larger volume of the solution comprising the proteolytically active compound, and advantageously also higher concentrations of the proteolytically active compound and longer reaction times compared to smaller samples are used. Using suitable cutting instruments, for example a microtome, tissue sections are prepared from fixed samples, where the thickness for examinations with a light microscope is generally from about 5 to 20 µm. Furthermore, the paraffinized sample may also be divided into smaller sample fragments using other methods, for example by punching with a hollow needle or by the laser capture method. Smaller tissue fragments require smaller amounts of the proteolytically active compound and shorter reaction times. Decisive here is in particular the thickness of the section, as this is the limiting factor for complete contact of the tissue with the proteolytically active compound. Preference is therefore given to using tissue sections having a thickness of preferably from 5 µm to 50 µm or smaller tissue fragments which, if appropriate, are obtained by dividing or homogenizing a larger sample.

The fixation time, i.e. the time the fixing agent acts on the biological sample, affects the degree of covalent crosslinking of the biomolecules in the biological sample, the degree of crosslinking increasing with longer fixation times. In samples which have been fixed only briefly, there is thus only a small degree of crosslinking of the biomolecules, which permits easier and faster dissolution of individual biomolecules. In contrast, samples which have been fixed for a long period of time have a high degree of crosslinking, which may delay the dissolution of larger biomolecules in particular. Accordingly, for strongly fixed (overfixed) samples it may be advantageous to have a longer reaction time of the proteolytically active compound. Here, the terms "fixed briefly" and "fixed for a long period of time" are to be understood relatively, since the optimum fixation time depends on the size of the piece of tissue. The diffusion rate of formalin in tissue is initially about 1 mm/h, the rate decreasing with increasing tissue depth. Thus, for a piece of tissue of a thickness of about 5 mm, about 8 h are required for complete penetration of the sample with formalin (fixation time). In practice, a fixation time of about 12-24 h is customary; very small samples require a much shorter fixation time and would already be overfixed at a fixation time of 12 h.

The optimum reaction time thus depends on sample-specific parameters such as fixation and fixation time, nature, amount and thickness of the biological sample and can be adjusted optimally for each individual sample. Surprisingly, it is nevertheless also possible to adjust the conditions such that for many possible sample parameters, i.e. for many different individual samples they allow the separation of DNA and RNA into undissolved and dissolved fraction. Here, the reaction time may be between 30 seconds and a number of days, preferably between one minute and 5 hours and especially preferably between 5 and 90 minutes and more preferably between 10 and 30 minutes. When 10 to 40 µl of a proteinase K solution of an activity of >600 mAU/ml are used at an incubation temperature of 56° C. and a reaction time of about 15 to 90 min for FFPE tissue section of a thickness from 10 to 20 µm, very good results are obtained for partial dissolution of the sample for the purpose of the invention, i.e. the RNA has been dissolved (almost) completely from the undissolved fraction and has passed into the dissolved fraction, whereas the DNA is still (almost) completely in the undissolved fraction (Examples 2 and 3).

According to one embodiment, step a) comprises the partial dissolution of the sample in an aqueous buffer solution comprising a detergent, preferably a non-ionic detergent, with simultaneous partial proteolysis of the protein-containing components of the sample using a proteolytically active enzyme, preferably a protease such as proteinase K, wherein the reaction is carried out at a temperature between 18° C. and 80° C., preferably 50 and 65° C. for a reaction time between 10 minutes and 5 hours, preferably between 10 and 90 minutes, more preferred between 10 to 30 minutes. This embodiment has the advantage that is fast and effective in releasing the RNA into the dissolved fraction.

Here, fixation of the biological sample can be effected with any fixative known to the person skilled in the art, in particular with acids, alcohols, ketones or other organic substances, such as, in particular, glutaraldehyde or formaldehyde, wherein biological samples fixed with formaldehyde being particularly preferred. According to a particularly preferred embodiment of the process according to the invention, a formaldehyde-fixed, paraffin-embedded biological sample (FFPE sample) is used.

If a biological sample embedded in paraffin is used, the paraffin is preferably initially removed at least partially, preferably completely, from the sample. The deparaffinization serves to selectively remove the paraffin used for embedding the biological sample to make the sample accessible to efficient lysis in an aqueous medium. In general, paraffin may interfere both during the dissolution and fractionation of the nucleic acids and during further purification and analysis of the nucleic acids. The deparaffination which is preferably carried out beforehand may have a marked effect on the quality, in particular the solidity, of the pellet obtained in the process according to the invention following the protease treatment, and thus on the separation of the nucleic acids and the obtainable yields.

The removal of the paraffin from the biological sample may in principle take place by any process for the deparaffinization of biological samples known to the person skilled in the art. Preferably, the deparaffinization is carried out by initially bringing the sample into contact with a hydrophobic organic solvent. Here, it may also be advantageous to mix the mixture of the biological sample and the organic solvent with agitation, for example by shaking on a laboratory shaker, employing a magnetic stirrer etc. to ensure effective dissolution of the paraffin from the sample. Advantageously, the sample is subsequently centrifuged to separate the paraffin dissolved in the organic solvent from the pellet, i.e. the biological sample. If required, the step of dissolving the paraffin from the biological sample may be repeated once, twice, three or up to ten times. The deparaffinization may preferably be carried out by incubation in hydrophobic organic solvents, with preference in an aromatic hydrocarbon, in particular in xylene, followed by rehydration of the sample in ethanol, as described, for example, in the application WO 2007/068764. Other organic solvents, such as, for example, alkanes, preferably alkanes which are liquid at room temperature of the general formula $C_nH_{2n+2}$ where 6<n<17 or mixtures of these, particularly preferably heptane, if appropriate with addition of $C_1$-$C_5$-alcohols, i.e. methanol, ethanol, propanol, isopropanol, n-butanol, isobutanol, n-pentanol, preferably methanol may also be used for deparaffinization. If straight-chain, i.d. unbranched, alkanes are used, n is preferably more than 6 and less than 17, since some of the alkanes of a chain length of six or less carbon atoms, some of them have to be classified as toxic, are gaseous at room temperature and/or are too volatile, and alkanes of a chain length of 17 and more carbon atoms are solid at room temperature. It is furthermore also possible to use mixtures of alkanes, if appropriate also with other compounds such as alkenes, aromatic compounds etc., as long as these are liquid at room temperature and dissolve paraffin, such as, for example, mineral oil. Deparaffinization by incubation in alkanes having a chain length of more than 6 and less than 17 carbon atoms, particularly preferably in heptane, has been found to be particularly advantageous for the subsequent separation of soluble and insoluble fractions A and B by the process according to the invention. Addition of a $C_1$-$C_5$-alcohol, preferably methanol, in an amount of 1-25% by volume, preferably 5-10% by volume, to the hydrophobic organic solvent may promote precipitation of the insoluble residue, thus making the separation of soluble and insoluble fraction easier and more efficient. In a preferred embodiment, the process therefore comprises, prior to the partial dissolution according to step (a), a step (i) for the selective removal of the paraffin, preferably by bringing the sample into contact with a hydrophobic organic solvent, particularly preferably using an apolar aliphatic or aromatic hydrocarbon of a chain length of more than 6 and less than 17 carbon atoms; in particular a hydrocarbon selected from the group comprising xylene, heptane and mineral oil, if appropriate with addition of a $C_1$-$C_5$-alcohol, preferably methanol, in an amount of 1-25% by volume, preferably 5-10% by volume. According to one embodiment, depraffinization is achieved by incubation with an alkane, preferably heptan, and an alcohol, preferably methanol. In addition to the dissolution of the paraffin with a suitable organic solvent, other processes are also suitable as processes for deparaffinization, such as, for example, melting the paraffin, as described by Banerjee et al. in *Biotechniques*, 18 (1995) pp. 768-773.

After the removal of the paraffin, it may be preferred to rehydrate the biological sample, this rehydration preferably being effected by stepwise washing with aqueous alcohol solutions of decreasing alcohol concentrations (descending alcohol series), with $C_1$- to $C_5$-alcohols being preferred and methanol, ethanol and isopropanol being particularly preferred. If the deparaffinization reagent used is xylene, the sample is usually rehydrated in this manner prior to further processing, the necessity of this rehydration for a subsequent nucleic acid isolation being disputed in the relevant literature. If the deparaffinization reagent used is a straight-chain aliphatic alkane, rehydration of the sample is not required. However, it is also possible to carry out deparaffinization and rehydration with a single suitable reagent, for example with the commercially available product EZ-DEWAX® from BIoGEnex, California, USA.

Preferably the sample is, after deparaffinization and rehydration, initially dried, for example by exposure to air or incubation in a drying oven. Furthermore, the optionally deparaffinised and rehydrated biological sample may preferably be homogenised prior to partial lysis, which is advantageous in particular in the case of relatively large tissue samples. In contrast, tissue sections up to a thickness of 20 μm do not generally require homogenization of the samples. This homogenization can be carried out using any apparatus known to the person skilled in the art for comminuting a biological sample, in particular a high-pressure cell digestion with the aid of a mechanical comminuting apparatus, for example a mill, a rotor-stator homogeniser, an Ultra-Turrax homogeniser or a fine cannula, or by ultrasound homogenisers.

In a preferred embodiment the process therefore comprises, after removal of the paraffin according to step (i) and before the partial dissolution of the sample in the aqueous buffer solution according to step (a), preferably at least one of the following steps:
  (ii) rehydration of the sample, preferably by repeated washing of the sample with aqueous $C_1$- to $C_5$-alcohol solutions of successively increasing water content,
  (iii) drying of the sample and/or
  (iv) homogenization of the sample.

Respective method steps to deparaffinise and work up the deparaffinised sample are also well-known in the prior art and thus, need no further description here.

According to one embodiment, the sample fixed by cross-linking is obtained in form of a pellet after deparaffinization. Preferably, the aqueous buffer solution is added to said pellet for performing the partial dissolution step a). According to a further embodiment, the deparaffinised sample comprising the deparaffinisation chemistry, respectively the deparaffinisation solution, is mixed with the aqueous buffer solution for use in step a), thereby forming an aqueous phase which is subjected in step a) to partial proteolysis of the protein-containing components of the sample using at least one proteolytically active compound to selectively release the comprised RNA into an dissolved fraction, while the comprised DNA predominantly remains in the undissolved fraction. Here, the proteolytically active compound, preferably the proteolytic enzyme, can be added to the aqueous phase while the solution used for deparaffinization is still on top of the aqueous phase that was formed due to the addition of the aqueous buffer solution. If performing the separation step b) in this alternative e.g. by centrifuging the partially digested cross-linked sample (see e.g. above and below), the mainly DNA containing undissolved fraction will form a pellet within the aqueous phase. To separate the dissolved from the undissolved fraction, the aqueous phase is e.g. collected through the deparaffinization solution e.g. by using a pipette, while leaving the undissolved, mainly DNA containing pellet behind. Alternatively, the deparaffinisation solution can be separated from the aqueous phase that is obtained after the addition of the aqueous buffer solution before adding the proteolytically active compound and separating the undissolved fraction from the dissolved fraction.

In step b) of the process according to the invention, the different types of nucleic acid present in the starting material, i.e. RNA and DNA, are then separated into a dissolved fraction (A), which contains predominantly the RNA, and an undissolved fraction (B), which contains predominantly the DNA. It is also possible to separate the entire sample including the dissolved and undissolved components into at least two fractions from which various biomolecules are then isolated or purified or in which various biomolecules may then be detected or analyzed; however, the sample is, after step a) of the process according to the invention, preferably separated into at least one dissolved fraction (A) and at least one undissolved fraction (B). The advantage of separating the two fractions is that from these two fractions in each case separately essentially one type of nucleic acid can be isolated without any need for separating the original biological sample, which would reduce the respective yield or result in an uneven distribution of the various cell types of a sample.

The fractions obtained in this manner can then be subjected separately to nucleic acid purification. It is also within the scope of the present invention to isolate the nucleic acid only from one fraction and discard the other fraction (see e.g. examples 6 and 7). During the further processing of the sample(s) for isolation of the nucleic acids, the sample(s) is/are preferably heated in the presence of a proteolytically active compound to a temperature in the range of 50-100° C., preferably of 55 to 95° C., particularly preferably of 60 to 90° C. and in particular of 65 to 85° C.

The separation of the undissolved components from the aqueous solution preferably is supported by cooling the mixture after the reaction time of the proteolytically active compound, in particular if the proteolytically active compound is active at elevated temperatures, i.e. temperatures above room temperature. Cooling is preferably carried out by incubating the sample at a temperature below the temperature of the protease digestion, preferably at room temperature, in particular at 4° C. or at even lower temperatures such as, for example, −20° C. or −80° C., where cooling at these temperatures is brief to avoid freezing of the entire aqueous solution. Thus, cooling is preferably carried out at a temperature of 15° C. or less, 10° C. or less, 4° C. or less or at even lower temperatures such as, for example, −20° C. or −80° C. Cooling can be performed before and/or during the separation step. Cooling has the advantage that the separation of the undissolved fraction, in particular the pelleting, is more efficient. This is in particular advantageous because FFPE samples usually comprise undissolved components, in particular DNA being cross-linked to proteins, rather than large amounts of solid components. Said undissolved components are usually difficult to pellet. Cooling assists the pelleting of the undissolved components and thus makes the separation more efficient. Thus, cooling results in that the mainly DNA containing undissolved fraction comprises more DNA and accordingly, the RNA containing dissolved fraction comprises less DNA contamination due to the improved separation of the individual fractions. This is particularly advantageous when processing cross-linked samples comprising little cell material.

According to one embodiment, separation results in that the mainly DNA containing undissolved fraction is obtained in form of a compact pellet. This allows to easily separate the mainly DNA containing pellet from the mainly RNA containing dissolved fraction.

In a third step, the dissolved fraction (A) and the undissolved fraction (B) obtained in this manner can be used separately from one another to a purification of the biomolecules present, preferably the nucleic acid(s). Here, the dissolved fraction (A) is preferably used for isolating the RNA, and the undissolved fraction (B) is preferably used for isolating the DNA. It is also within the scope of the present invention to isolate the nucleic acid only from one fraction and discard the other fraction (see e.g. examples 6 and 7).

Here, the dissolved fraction (A) can be used directly, without further lysis, in a suitable process for nucleic acid isolation. However, a further lysis, for example with proteolytically active compounds, preferably proteases, may optionally be carried out in the aqueous solution. Suitable processes are all processes and methods for isolating nucleic acids, in particular RNA, known to the person skilled in the art. Suitable are processes for isolating nucleic acids from fixed sample material, as described in the applications WO 2007/068764, WO 2008/021419, WO 2005/012523 or WO 2005/054466, or else processes carried out with the aid of the commercial kits RNeasy FFPE and miRNeasy FFPE (both from QIAGEN). In the latter case, fraction A is subjected to at least one heating step before the nucleic acids are purified by chaotrope-mediated binding to a silica membrane. Further extraction and purification of the RNA can preferably be carried out with the aid of the process described in the application WO 2007/068764. If a process as described in the application WO 2007/068764 is used for the isolation of nucleic acids from the dissolved fraction, the sample is heated in the presence of a nucleophilic reagent. This can be carried out in the aqueous solution comprising at least one proteolytically active compound and the now dissolved nucleic acids, where the nucleophilic reagent required for the process described in the application WO 2007/068764 can be added after step a) of the process according to the invention (action of the proteolytically active compound) to the aqueous solution or even be present in the aqueous solution before the addition to the sample according to step a). The separation of the fractions can be carried out after heating of the samples as described in the application WO 2007/068764 or, preferably, directly after the action of the proteolytically active compound, prior to further heating.

Suitable nucleophilic reagents are all Lewis bases capable of transferring electrons into an empty orbital or into empty orbitals of a Lewis acid. From among these Lewis bases, particular preference is given to reagents having at least one functional group which carries a negative charge, is negatively polarized or has at least one free electron pair.

Compounds comprising a functional group having a negative charge are, for example, alkali metal or alkaline earth metal alkoxides, alkali metal or alkaline earth metal hydroxides, alkali metal or alkaline earth metal halides, alkali metal or alkaline earth metal cyanides and the like, without being limited thereto.

Reagents having at least one functional group which is negatively polarized are in particular those reagents which have at least one functional group which contains two atoms which are covalently attached to one another and whose electronegativity according to Alfred and Rochow differs by at least 0.25, preferably by at least 0.5 and more preferably by at least 1.0.

However, particular preference according to the invention is given to nucleophilic reagents having at least one functional group having one or two, particularly preferably one, free electron pair(s), and from among these compounds most preference is in turn given to those having at least one primary, secondary or tertiary amino group of the structure I

(I)

in which $R^1$ is a $C_1$- to $C_{20}$-hydrocarbon group, particularly preferably a $C_2$- to $C_{15}$-hydrocarbon group and more preferably a $C_2$- to $C_{10}$-hydrocarbon group, a $C_1$- to $C_{20}$-hydrocarbon group which has at least one heteroatom, a $C_2$- to $C_{15}$-hydrocarbon group which has at least one heteroatom and more preferably a $C_2$- to $C_{10}$-hydrocarbon group which has at least one heteroatom or an optionally heteroatom-substituted aromatic ring system, $R^2$ is a $C_1$- to $C_{20}$-alkyl group, particularly preferably a $C_1$- to $C_{10}$-alkyl group and more preferably a $C_1$- to $C_2$-alkyl group, in particular a methyl group or an ethyl group, a $C_1$- to $C_{20}$-hydroxyalkyl group, particularly preferably a $C_1$- to $C_{10}$-hydroxyalkyl group and more preferably a $C_1$- to $C_2$-hydroxyalkyl group or a hydrogen atom, a hydrogen atom being most preferred, and $R^3$ is a $C_1$- to $C_{20}$-alkyl group, particularly preferably a $C_1$- to $C_{10}$-alkyl group and more preferably a $C_1$- to $C_2$-alkyl group, in particular a methyl group or an ethyl group, a $C_1$- to $C_{20}$-hydroxyalkyl group, particularly preferably a $C_1$- to $C_{10}$-hydroxyalkyl group and more preferably a $C_1$- to $C_2$-hydroxyalkyl group or a hydrogen atom, a hydrogen atom being most preferred.

According to the invention, particular preference is given to nucleophilic reagents having a functional group of the structure I shown above which have in particular at least one functional group of the structure I in which at least one of the radicals $R^2$ and $R^3$, most preferably both radicals $R^2$ and $R^3$, is a hydrogen atom/are hydrogen atoms. In addition, particular preference is given to those nucleophilic reagents which have at least one functional group of the structure I in which the nitrogen atom is only covalently attached to sp3-hybridized atoms in the radicals $R^1$, $R^2$ and $R^3$. In particular, none of the radicals $R^1$, $R^2$ or $R^3$ should be capable of delocalising the free electron pair at the nitrogen atom over the radicals $R^1$, $R^2$ and $R^3$, respectively. Thus, particularly preferably, none of the radicals $R^1$, $R^2$ and $R^3$ should, for example, have the structure II.

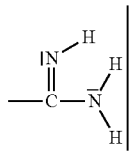

II

Particular preference according to the invention is given to nucleophilic reagents having at least one functional group of the structure I selected from the group comprising methylamine, ethylamine, ethanolamine, n-propylamine, n-butylamine, isobutylamine, tert-butylamine, dimethylamine, diethylamine, diethanolamine, di-n-propylamine, diisopropylamine, dibutylamine, trimethylamine, triethylamine, triethanol-amine, hexamethylenetetramine, 2-ethylhexylamine, 2-amino-1,3-propanediol, hexylamine, cyclohexylamine, 1,2-dimethoxypropanamine, 1-aminopentane, 2-methyloxypropylamine, tri(hydroxymethyl)aminomethane, aminocarboxylic acids, in particular glycine or histidine, or aminoguanidine, where the last mentioned is possible, however, not preferred. Among these most preference is given to ethanolamine, diethanolamine, triethanolamine, amino-1,3-propanediol and tri(hydroxymethyl)aminomethane. Preferred nucleophilic reagents having at least one functional group of the structure I are furthermore aromatic amines selected from the group comprising aniline, toluidine, naphthylamine, benzylamine, xylidine, xylenediamines, naphthalenediamines, toluenediamines, 3,3'-dimethyl-4,4'-diphenyldiamine, phenylenediamines, 2,4'-methylenedianiline, 4,4'-methylenedianiline, sulphonyldianiline and dimethylbenzylamine.

According to a particular embodiment of the process according to the invention where the nucleophilic reagent has at least one primary amino group of the structure I, the nucleophilic reagent is a $C_1$- to $C_6$-alkylamine, a $C_1$- to $C_6$-alkyldiamine, a $C_1$- to $C_6$-alkyltriamine, a $C_1$- to $C_{15}$-aminoalkohol, a $C_1$- to $C_{15}$-aminodiol or a $C_1$- to $C_{15}$-aminocarboxylic acid.

According to another particular embodiment of the process according to the invention the nucleophilic reagent is a heterocyclic compound which comprises a nitrogen atom and is selected from the group comprising pyrrole, pyridine, quinoline, indole, azacyclopentane, azacyclohexane, morpholine, piperidine, imidazole or a derivative of these compounds, where a derivative of these compounds is preferably understood as meaning a compound having, instead of a hydrogen atom, a $C_1$- to $C_3$-alkyl group, particularly preferably a methyl or an ethyl group, attached at one or more carbon atoms or at the nitrogen atom in the compounds mentioned above.

From among the nucleophilic reagents mentioned above, preference is given to those which are water-soluble, in particular those which have a solubility of at least 1 g/l, particularly preferably at least 10 g/l and more preferably at least 100 g/l in water at a temperature of 25° C. and at a pH of 7.

The concentration of the nucleophilic reagent in the aqueous solution used is preferably in a range of from 0.1 to 10 000 mmol/l, more preferably from 1 to 5000 mmol/l, even more preferably from 5 to 2500 mmol/l and most preferably from 20 to 1000 mmol/l. According to a particularly advantageous embodiment of the process according to the invention, the concentration of the nucleophilic reagent in the aqueous solution is more than 20 mmol/l, particularly preferably more than 50 mmol/l and most preferably more than 100 mmol/l.

According to one embodiment, after performing the digest with the proteolytically active compound, which preferably is a proteolytic enzyme, the cross-links in the sample are at least partially reversed by heating, preferably to a temperature of at least 70° C., more preferred at least 75° C., most preferred at least 80° C. or at least 90° C. for a time period of at least 5 min, preferably at least 10 min, most preferred at least 15 min. Heating to 80° C. for at least 15 min is particularly preferred for reversing the cross-links in the RNA containing dissolved fraction of the degraded sample. Heating to at least 85° C., preferably at least 90° C. for at least 30 min up to several hours, preferably at least 1.5 or at least 2 hours, is preferred for reversing the cross-links in DNA. As described above, heating is carried out in the presence of a nucleophilic reagent. Suitable incubation times are also described in the cited prior art. This additional heating step to reverse the cross-links can be performed before or after separating the mainly RNA containing dissolved fraction from the mainly DNA containing undissolved fraction. It is preferred, in particular if it is also intended to isolate the DNA subsequently from the undissolved fraction, to perform said heating step after separating the fractions because this heating step might result in that further DNA is released from the undissolved fraction. If it is only intended to isolate the RNA, said heating step may also be performed prior to separating the fractions, because additionally released DNA can be degraded e.g. by performing a DNase digest. A preferred embodiment for performing the DNase digest which also preserves small RNA molecules is described in detail below.

According to one embodiment a DNase digest is performed on the separated, mainly RNA containing dissolved fraction. Separating the undissolved fraction which comprises the main amount of the DNA comprised in the cross-linked sample already removes the main portion of the DNA comprised in said sample. Thus, the mainly RNA containing dissolved fraction that is obtained after partial digestion and separation of the fractions is already DNA depleted. Remaining amounts of DNA that might have been released during the partial digestion in step a) can be efficiently degraded by performing a DNase digest on the RNA containing dissolved fraction. Isolating the RNA from the DNase digested sample provides pure RNA which comprises little to no DNA contaminations.

Thus, according to one embodiment, DNase is added to the separated, mainly RNA containing dissolved fraction. It was very surprising that the DNase digest can be performed efficiently prior to isolating the RNA. This, as it was assumed that the DNase could not function efficiently as the common prior art methods isolate the RNA prior to performing the DNase digest when purifying RNA. Furthermore, performing a DNase digest prior to isolating the RNA also has considerably advantages because e.g. compared to the common on-column DNase treatment, the amount of in particular small RNA is increased when using the process according to the present invention. A respective DNase digest is performed in examples 6 and 7. Preferably, the DNase digest is performed after the cross-links were reversed by heating as is described above.

The term "DNase" refers to any enzyme which catalyses the hydrolytic cleavage of phosphodiester linkages in the DNA. A wide variety of deoxyribonucleases are known, which differ in their substrate specificities, chemical mechanisms, and biological functions. The term "DNase" refers to exodeoxyribonucleases as well as endodeoxyribonucleases. In particular, DNase I and DNase II can be used. DNase I is preferred.

The DNase digest is performed under conditions wherein the DNase is active to allow an efficient degradation of the DNA. The efficency of the DNase digest can be e.g. controlled by the amount of DNase added to the degraded sample and furthermore, by the addition of additives which promote the activity of the DNase such as in particular Mg and Ca ions. Furthermore, depending on the conditions used for achieving partial digestion in step a), intermediate processing steps might be advantageous to ensure that the DNase digest works with high efficiency on the separated, mainly RNA containing dissolved fraction. E.g., components that could interfere with the DNase digest can be removed or diluted to a concentration which does not inhibit the DNase digest. The DNase digest is performed in the presence of Mg and Ca ions in concentrations at which the DNase is active. E.g. for performing the DNase digest, Mg and Ca ions can be added to the degraded sample e.g. in the form of $MgCl_2$ and $CaCl_2$ to establish suitable concentrations in the DNase digestion mixture. The suitable concentrations of Mg and Ca ions depend on the sample and in particular the lysis conditions used in degradation step a). E.g. if Ca and Mg ions are already provided during digestion in step a) and thus, are present in the degraded sample, less amounts of Mg and Ca ions must be added for the DNase digest or the addition of Mg and Ca is not even necessary. The use of higher concentrations of Mg and Ca ions during the DNase digest is advisable, if chelating agents such as e.g. EDTA were used during step a). According to one embodiment, the Mg ions and the Ca ions are provided in the reaction composition, preferably in the form of $MgCl_2$ and $CaCl_2$, in a concentration selected from the group consisting of at least 0.2 mM each, at least 2 mM each, at least 5 mM each, at least 7.5 mM each and preferably at least 10 mM each. Furthermore, the Ca and Mg ions can be provided in a concentration range for each ion that is selected from the group consisting of 0.2 mM to 1M, 2 mM to 100 mM, 10 mM to 50 mM and 10 mM to 25 mM. The DNase digest reaction composition comprising the DNase, the degraded sample and optionally, further additives that promote the DNase digest is incubated for a suitable time to allow the DNA to be degraded. Preferably, the incubation occurs for at least 5 min, at least preferably 10 min or at least 15 min. Suitable ranges include 1 min to 6 hours, 5 to 120 min, 10 to 60 min and 15 to 30 min. After performing the optional DNase digest, the RNA can be isolated from the sample. As discussed herein, basically any RNA isolation method can be used.

According to one embodiment, the RNA is isolated from the dissolved, optionally DNase treated fraction by establishing suitable binding conditions by adding appropriate additives and binding the RNA to a nucleic acid binding solid phase. According to one embodiment, isolation of the RNA comprises at least the following steps:
  i) adding at least one alcohol and/or at least one chaotropic agent and optionally further additives to form a binding mixture and contacting the binding mixture with a nucleic acid binding solid phase to bind the RNA to said solid phase;
  ii) optionally washing the RNA while it is bound to the solid phase; and
  iii) optionally eluting the RNA from the solid phase.

As nucleic acid binding solid phase, any material that is capable of binding nucleic acids can be used and thus includes a variety of materials that are capable of binding nucleic acids under suitable conditions. Exemplary solid phases that can be used in conjunction with the present invention include, but are not limited to, compounds comprising silica and siliceous solid phases, including but not limited to, silica particles, silicon dioxide, diatomaceous earth, glass, alkylsilica, aluminum silicate, and borosilicate; nitrocellulose; diazotized paper; hydroxyapatite (also referred to as hydroxyl apatite); nylon; metal oxides; zirconia; alumina; polymeric supports, diethylaminoethyl- and triethylaminoethyl-derivatized supports, hydrophobic chromatography resins (such as phenyl- or octyl Sepharose) and the like. The term solid phase is not intended to imply any limitation regarding its form or design. Thus, the term solid phase encompasses appropriate materials that are porous or non-porous; permeable or impermeable; including but not limited to membranes, filters, sheets, particles, magnetic particles, beads, gels, powders, fibers, and the like. According to one embodiment, the surface of the solid phase is not modified and is, e.g., not modified with functional groups. According to a preferred embodiment, the nucleic acid binding solid phase is comprised in a column. The term "column" as used herein in particular describes a container having at least two openings. Thereby, a solution and/or sample can pass through said column. The term "column" in particular does not imply any restrictions with respect to the shape of the container which can be e.g. round or angular and preferably is cylindrical. However, also other shapes can be used, in particular when using multi-columns. The column comprises the nucleic acid binding solid phase. Said solid phase that is comprised in said column should allow the passage of a solution, respectively the sample when applied to the column. This means that if e.g. a centrifuge force is applied to the column, a solution and/or the sample is enabled to pass through the column in direction of the centrifuge force. As discussed above, when using a respective column based nucleic acid isolation procedure, the sample is usually passed through the column, e.g. assisted by centrifugation or vacuum, and the nucleic acids bind to the comprised nucleic acid solid phase during said passage. The column can be used in a single format or in a multi-format. Such multi-columns having a similar format as multi-well plates and which comprise a nucleic acid binding solid phase such as a membrane, are well-known in the prior art. Preferably, the column is a spin column. As nucleic acid binding solid phase comprised in the column, any solid phase can be used that is usually utilized in column based nucleic acid isolation procedures. Preferably, a nucleic acid binding membrane, and thus a membrane that is capable of binding nucleic acids is used. Suitable membranes include but are not limited to hydrophilic membranes, hydrophobic membranes and membranes which bind nucleic acids via ion exchange. Examples include but are not limited to silica membranes, glass fiber membranes, nylon membranes, cellulose membranes such as nitrocellulose membranes, modified cellulose membranes (e.g. acetyl- or hydroxy-), paper membranes, in particular modified papers. Preferably, the membrane is porous. Furthermore, it is preferred to use a membrane comprising or consisting of silica. A further common nucleic acid binding solid phase comprised in a column is a fill of nucleic acid binding particles, such as silica particles, or a layer of a nucleic acid binding material (e.g. a silica gel). E.g. the silica particles can be arranged as a layer on an inert filter or membrane, thereby forming a nucleic acid binding solid phase.

To digest the undissolved components of the sample and to break the remaining crosslinks of the biomolecules, if appropriate, fraction (B), which comprises the undissolved components, is preferably subjected to a further treatment. The dissolvable nucleic acids, predominantly DNA, which are substantially still in the undissolved fraction (B), can be isolated by this further treatment step. Any process known for dissolving nucleic acids from fixed tissue is suitable, for example the processes as described in WO 2007/068764, WO 2008/021419, WO 2005/012523 or WO 2005/054466 or else the processes which can be carried out with the aid of commercially available kits, for example the QIAamp DNA FFPE Tissue Kits (QIAGEN), is suitable for isolating the nucleic acids, in particular the DNA, from the undissolved fraction (B). In the latter case, the undissolved components of fraction B are subjected to at least one further treatment with a proteolytic agent, for example a protease, and a heating step. The protease treatment effects efficient lysis and thus a release of the dissolvable nucleic acids. Since the undissolved fraction B compared to the complete fixed sample comprises in particular only the less readily dissolvable components, further optimization, for example an extension of the further protease step and of the heating step, may be advantageous and lead to markedly improved yields and results in subsequent (downstream) analyses.

Thus, according to one embodiment, the DNA is obtained from the undissolved, mainly DNA containing fraction after separation of the fractions. Obtaining the DNA from the undissolved fraction comprises according to one embodiment the following steps:

i) releasing the DNA from the undissolved, mainly DNA containing fraction by subjecting said undissolved fraction to lysis with simultaneous enzymatic protease digestion, wherein preferably, at least one detergent is used during lysis and optionally, further additives and wherein the enzymatic digestion is preferably supported by heating (suitable conditions are described above);

ii) heating the mainly DNA containing fraction to at least partially reverse the cross-links preferably by heating the sample preferably after step i) to a temperature of at least 70° C., more preferred at least 80° C., most preferred at least 85° C., more preferred at least 90° C. in the presence of a nucleophilic reagent and iii) isolating the DNA after reversing the cross-links, preferably by establishing binding conditions by adding appropriate additives and binding the DNA to a nucleic acid binding solid phase. Preferably, a chaotropic agent and a detergent, preferably a non-ionic detergent, and alcohol are added to establish the binding conditions. Suitable DNA isolating procedures are also well known in the prior art.

Thus, preferably, the process according to the invention comprises, subsequent to step b), further steps for the separate purification of the RNA obtained from fraction A and/or the DNA obtained from pellet B, preferably by precipitation, binding of the nucleic acids to suitable binding materials, electrophoresis and/or chromatography or combinations thereof.

Furthermore, the process preferably comprises a step for the analysis/detection of the isolated and/or purified nucleic acids.

All analysis methods known to the person skilled in the art, for example amplification techniques such as PCR, qPCR, RT-PCR, qRT-PCR and amplification of the entire genomic DNA (whole genome amplification), gel electrophoresis, blotting techniques, in particular Southern blotting and Northern blotting, microarray analyses, restriction fragment length polymorphism analyses (RFLP analyses), SAGE (serial analysis of gene expression), sequencing including NextGeneration sequencing and RNA sequencing, single nucleotide polymorphism analyses (SNP analyses), mutation analyses, epigenetic analyses, in particular analyses of methylation patterns or combinations thereof can be used for analyzing the nucleic acids isolated by the process according to the invention.

As becomes apparent from the above disclosure, the present invention also provides a process for obtaining RNA in a dissolved fraction and DNA in an undissolved fraction from the same biological sample fixed by crosslinking, comprising the following steps:

a) partial dissolution of the sample in an aqueous buffer solution with simultaneous partial proteolysis of the protein-containing components of the sample using at least one proteolytically active compound to obtain a dissolved fraction (fraction A) and an undissolved residue (pellet; fraction B), b) separation of the dissolved fraction from the undissolved residue, wherein the dissolved fraction comprises mainly RNA, based on the total amount of nucleic acids in the dissolved fraction, and the undissolved residue comprises mainly DNA, based on the total amount of nucleic acids in the undissolved residue.

According to one embodiment, the separation of the fraction comprising predominantly RNA from the fraction comprising predominantly DNA requires neither precipitation nor extraction of one or both types of nucleic acid with organic solvents nor selective binding of one or both types of nucleic acid to a solid matrix. According to one embodiment, after separation of the fractions, the RNA is isolated from the mainly RNA containing dissolved fraction and/or DNA is isolated from the mainly DNA containing undissolved fraction. The mainly DNA containing undissolved fraction can be discarded after separation, if e.g. only the isolation of RNA is intended.

Suitable and preferred embodiments as well as the advantages associated with the partial digestion and separation steps according to the present invention as well as suitable and preferred embodiments for the subsequent nucleic acid isolation were discussed in detail above with respect to the process for the parallel isolation and/or purification of RNA and DNA from the same cross-linked sample. It is referred to the above disclosure which also applies here.

The invention furthermore comprises a kit for carrying out the process according to the invention, comprising at least (1) a proteolytically active compound, preferably one of the proteolytically active compounds mentioned above, (2) at least one buffer substance, preferably one of the buffer substances mentioned above and (3) at least one surfactant, preferably one of the surfactants mentioned above, and also preferably (4) instructions for carrying out the incomplete proteolysis according to step (a).

In a particularly preferred embodiment, the kit according to the invention comprises furthermore (5) at least one nucleic acid-binding material and also optionally (6) buffers for nucleic acid isolation, preferably binding and/or elution buffers.

Suitable for use as nucleic acid-binding material (5) are all materials known to the person skilled in the art for adsorption of DNA or RNA, with particular preference being given to cellulose-based materials, in particular carboxy-funktional cellulose materials or diethylaminoethylcellulose, agarose, mineral carriers such as silica, glass, quartz, zeolites or metal oxides or ion exchanger material-coated carriers. The materials mentioned can be present, for example, in the form of membranes or magnetic or non-magnetic particles. The nucleic acid-binding material is preferably contained in the kit as column material in pre-fabricated columns or else as a suspension. The type of material depends crucially on the chemical structure of the nucleic acid to be analyzed, the person skilled in the art being familiar with the adsorption materials suitable in each case for the respective intended application, i.e. the analysis of RNA or DNA.

As elution buffer (6), the kit according to the invention may comprise any buffer known to the person skilled in the art and customarily used for elution of nucleic acids from nucleic acid binding materials. The elution buffer is preferably an aqueous salt solution, in particular an aqueous solution which comprises alkali metal halides, such as, for example, NaCl, KCl or LiCl, alkaline earth metal halides, such as, for example, $CaCl_2$ or $MgCl_2$, ammonium salts, such as, for example, ammonium chloride or ammonium sulphate, or mixtures of at least two of these salts, where the elution buffer may optionally also comprise buffer system on basis of, for example, alkali metal acetate/acetic acid or buffer systems based on tris(hydroxylmethyl)aminomethane. If the kit is to be used for isolating RNA from a fixed tissue and the matrix used is a silica membrane, it is particularly preferred to use water, in particular RNase-free water, as elution buffer.

As binding buffer (6), the kit according to the invention may comprise any buffer known to the person skilled in the art and customarily used for attaching nucleic acids to nucleic acid-binding materials, where the binding buffer has to be matched to the respective nucleic acid-binding material used. If the nucleic acid-binding material used is a silica matrix, the binding buffer preferably comprises chaotropic agents and optionally additionally a $C_1$-$C_5$-alcohol.

The kit according to the invention can be used for analyzing and/or quantifying nucleic acids present in biological samples, i.e. both DNA and RNA.

For this reason, the kit according to the invention can furthermore be employed for the diagnosis, prognosis, decisions with respect to therapy and/or the monitoring of the therapy of a disease of samples outside a human or animal body.

EXAMPLES

Example 1

Figure 1:
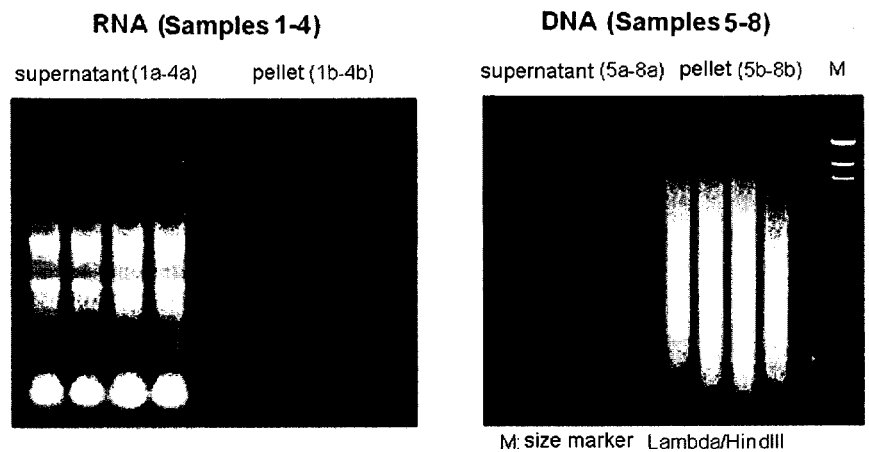
FIG. 1 shows the separation of RNA and DNA samples isolated by the process according to the invention from the supernatant and the pellet, respectively, on TAE-agarose gels (DNA) and formaldehyde-agarose gels (RNA), respectively, after staining with ethidium bromide (Example 1). For size comparison, the size marker Lambda/HindIII (Invitrogen, Carlsbad, Calif., USA) was applied in lane M.

Separation of RNA and DNA by the Process According to the Invention

The samples used were formalin-fixed and paraffin-embedded tissue samples (FFPE samples) from rat liver which had been stored at room temperature for about 4 months after embedding. With the aid of a microtome, sections of a thickness of about 20 μm were prepared from these samples. In each case, one section per reaction was used. Components of the RNeasy FFPE kit and the QIAamp FFPE kit from QIAGEN were employed for the subsequent isolation of DNA and RNA from the processed samples.

For deparaffinization, the tissues were initially incubated in 1 ml of xylene for 10 min. After pelletization by centrifugation of the sample and removal of the supernatant, this treatment with xylene was repeated two more times. The samples were subsequently treated in each case twice with anhydrous ethanol followed by aqueous ethanol solutions (first 96% ethanol and then 70% ethanol) and dried at 37° C. for 10 min.

The deparaffinized sample pellets obtained in this manner were treated with 150 μl of an aqueous solution comprising 20 mM Tris, 2 mM EDTA and 0.2% SDS (w/v) (pH 7) and mixed with 10 μl of a proteinase K solution (>600 mAU/ml) as proteolytically active compound. The mixture obtained was incubated at 56° C. with shaking at 1400 rpm for 15 min. To separate the dissolved fraction (A) from the undissolved fraction (B), the samples were centrifuged and the supernatant (fraction A) was removed from the pellet which contained the undissolved components (fraction B).

To determine the distribution of the types of nucleic acid, RNA and DNA, in the two fractions, the RNA from supernatant and pellet was isolated from in each case 4 samples (samples 1-4), and from a further 4 samples (samples 5-8) the DNA from supernatant and pellet was isolated.

To isolate the RNA from the supernatant (fraction A) of samples 1-4 (samples 1a to 4a), the supernatant was incubated at 80° C. for 15 min. To adjust to conditions for DNA binding, 320 μl of a chaotropic buffer, for example the RBC buffer from QIAGEN, were added. The mixture was applied to a silica membrane, for example present in the gDNA eliminator column from QIAGEN, and passed through the membrane by centrifugation at 14 000 rpm for 1 min. Since the composition of the mixture leads to selective binding of the DNA to the silica membrane, the RNA is in the eluate of the column. To adjust to binding conditions for RNA, this eluate was mixed with ethanol and then once more applied to a silica membrane, for example present in the RNeasy MinElute column from QIAGEN, and passed through the membrane by centrifugation at 14 000 rpm for 1 min. The silica membrane was then washed twice with in each case 500 μl of the alcohol-containing wash buffer RW2 (QIAGEN). The membrane was dried by 5 minutes of centrifugation at 14 000 rpm, and the RNA was, after a 1-minute incubation, eluted with 30 µl of water.

To isolate the RNA from the pellet (fraction B) of samples 1-4 (samples 1b to 4b), the pellet was mixed with 150 µl of the PKD buffer from QIAGEN, which comprises a surfactant and a nucleophilic reagent, and 10 µl of proteinase K from QIAGEN. After 15 minutes of incubation at 56° C. and then 15 minutes of incubation at 80° C., the lysate was treated with a chaotrope-containing binding buffer, for example the RBC buffer from QIAGEN, and the mixture was applied to a silica membrane, for example present in the RNeasy MinElute column from QIAGEN, and passed through the membrane by centrifugation at 10 000 rpm for 1 min. As described above, the silica membrane was washed twice with the wash buffer RW2, and the RNA was eluted.

To isolate the DNA from the supernatant (fraction A) of samples 5-8 (samples 5a to 8a), the supernatant was made up to a total volume of 180 µl with the surfactant-containing lysis buffer ATL (QIAGEN), and 20 µl of proteinase K from QIAGEN were added. The samples were incubated at 56° C. with shaking at 1400 rpm for 1 hour and then heated at 90° C. for 1 hour. To degrade any RNA present, after the incubation 4 µl of a RNAse A solution (100 mg/ml) were mixed into the sample. For further purification of the DNA, the samples were mixed with in each case 200 µl of a chaotropic buffer, for example the AL buffer from QIAGEN, and ethanol. The mixture was applied to a silica membrane, for example present in the QIAamp MinElute column from QIAGEN, and passed though the membrane by centrifugation at 10 000 rpm for 1 min. The silica membrane was then washed with 500 µl of the guanidine salt-comprising wash buffer AW1 and then with 500 µl of the alcohol-containing wash buffer AW2 from QIAGEN. The membrane was dried by a two-minute centrifugation at 14 000 rpm, and the DNA was, after a one-minute incubation, eluted by centrifugation with 30 µl of a DNA elution buffer, for example the buffer ATE from QIAGEN.

To isolate the DNA from the pellet (fraction B) of samples 5-8 (samples 5b to 8b), the pellet was treated with a customary DNA lysis buffer, such as, for example, 180 µl of the surfactant-comprising buffer ATL from QIAGEN. Since the pellet only contained components which had not yet been dissolved by the prior treatment, an additional lysis with 20 µl of proteinase K from QIAGEN was carried out to dissolve these undissolved components, too. After a one-hour incubation at 56° C. and a subsequent one-hour incubation at 90° C., the lysate was treated with a chaotrope-containing binding buffer, for example the AL buffer from QIAGEN, and also ethanol. The mixture was applied to a silica membrane, for example present in the QIAamp MinElute column from QIAGEN, and passed through the membrane by centrifugation at 10000 rpm for 1 min. As described above, the silica membrane was washed with the wash buffers AW1 and AW2, the membrane was dried and the DNA was eluted.

To determine the distribution of the nucleic acids isolated in this manner from the two fractions supernatant (A) and pellet (B), the nucleic acids of both fractions were quantified using suitable methods. The determination of the yield and purity of the DNA and RNA was carried out via the optical density (OD) by measuring the absorption of the sample at 260/280 nm. The yield is in each case stated in percent of the total yield. Here, the total yield is the sum of the yield of one type of nucleic acid in supernatant and pellet. Table 1 shows the mean values of four determinations.

TABLE 1

| | RNA (samples 1-4) | | DNA (samples 5-8) | |
|---|---|---|---|---|
| | yield % | OD (260/280) | yield % | OD (260/280) |
| supernatant (fraction A) | 91.9% | 1.96 | 20.5 | 1.96 |
| pellet (fraction B) | 8.1% | 1.69 | 79.5 | 1.79 |

For further analysis, in each case 10 µl of the nucleic acids isolated from the respective fractions were separated by customary methods on a TAE-agarose gel (Tris acetate/EDTA) in the case of DNA or on a formaldehyde/agarose gel in the case of RNA and stained with ethidium bromide. The result is shown in FIG. 1.

The results show that, when the process according to the invention is applied, there is a clear separation/fractionation of the nucleic acids prior to the subsequent purification. The RNA is located predominantly in the supernatant, whereas the DNA is located predominantly in the pellet fraction.

Example 2

Effect of the Amount of Proteolytically Active Compound Used

The samples used for this experiment were formalin-fixed and paraffin-embedded tissue samples (FFPE samples) from rat liver which had been stored at room temperature for about 7 months after embedding. With the aid of a microtome, sections of a thickness of about 10 µm were prepared from these samples. In each case, two sections per reaction were used. Components of the RNeasy FFPE kit and the QIAamp FFPE kit from QIAGEN were employed for the subsequent isolation of DNA and RNA from the processed samples.

For deparaffinization, the tissues were initially incubated in 1 ml of heptane each for 10 min. After addition of 50 µl of methanol and mixing the sample was centrifuged, the supernatant was removed and the residue was air-dried at room temperature for 5 min.

The deparaffinized sample pellets obtained in this manner were treated with 150 µl of an aqueous solution comprising 20 mM Tris, 2 mM EDTA and 0.2% SDS (pH 7) and mixed with 10 µl, 20 µl or 40 µl of a proteinase K solution (>600 mAU/ml) as proteolytically active compound. This mixture was incubated at 56° C. with shaking at 1400 rpm for 15 min. To separate the dissolved fraction (A) from the undissolved fraction (B), the samples were initially cooled on ice for 5 min and then centrifuged at 4° C. For further isolation of the RNA, the supernatant was removed and the pellet was discarded.

The supernatant was subsequently incubated at 80° C. for 15 min. To adjust to binding conditions, 320 µl of a chaotropic buffer, for example the RBC buffer from QIAGEN, were then added, and the mixture obtained was mixed with ethanol, applied to a silica membrane, for example present in the RNeasy MinElute column from QIAGEN, and passed through the membrane by centrifugation at 14 000 rpm for 1 min. The silica membrane was then washed twice by passing through 500 µl of the alcohol-containing wash buffer RW2. The membrane was dried by 5 minutes of centrifugation at 14 000 rpm. The RNA was then, after a 1-minute incubation, eluted by centrifugation by applying 30 µl of water.

To analyze the RNA isolated in this manner, the yield was determined by measuring the absorption at 260 nm. The results are shown in Table 2.

The integrity of the RNA was determined using an Agilent Bioanalyzer and stated in the form of the RIN value, where an RIN value of 10 represents completely intact RNA and an RIN value of 0 represents completely degraded RNA. The results are likewise shown in Table 2.

To examine the effect of different amounts of the proteolytically active compound not only on the isolation of the nucleic acids in the process according to the invention, but also on the subsequent analysis by amplification, the RNA was analyzed by quantitative real-time RT-PCR. To this end, the isolated RNA was, in each case in two determinations, used for detecting an amplicon of the madH7 transcript. The eluates were each diluted in a ratio of 1:10 with water. In each case 5 µl of these diluted solutions were used for the real-time-PCR. Amplification was carried out in a total volume of 25 µl with a mastermix suitable for real-time RT-PCR, such as, for example, the QuantiTect SYBRGreen RT-PCR kit from QIAGEN, according to the manufacturer's instructions. Amplification was carried out in a suitable real-time amplification instrument such as, for example, the ABI PRISM® 7900HT Sequence Detection System from Applied Biosystems (Carlsbad, Calif., USA). The measured ct values were used to determine the mean values, which are shown in Table 2.

TABLE 2

| Amount of proteinase K [µl] | RNA yield [µg] | RIN value | ct value |
|---|---|---|---|
| 10 | 14.77 | 7.2 | 25.7 |
| 20 | 14.09 | 7.6 | 25.2 |
| 40 | 13.42 | 7.3 | 25.1 |

The results show that all amounts of proteinase K used lead to comparable yields, comparable RNA integrity and comparable results in real-time RT-PCR. The amount of the proteolytically active compound in the process according to the invention can thus be varied within a wide range.

Example 3

Reaction Time of the Proteolytically Active Compound

The samples used for this experiment were formalin-fixed and paraffin-embedded tissue samples (FFPE samples) from rat liver which had been stored at room temperature for about 5 months after embedding. With the aid of a microtome, sections of a thickness of about 20 µm were prepared from these samples. In each case, one section per reaction was used. Components of the RNeasy FFPE kit and the QIAamp FFPE kit from QIAGEN were employed for the subsequent isolation of DNA and RNA from the processed samples.

Deparaffination, rehydration, and drying of the sections were performed as described in Example 1. The deparaffinized sample pellets obtained in this manner were treated with 150 µl of an aqueous solution comprising 20 mM Tris, 2 mM EDTA and 0.2% SDS (pH 7) and mixed with 10 µl of a proteinase K solution (>600 mAU/ml) as proteolytically active compound. This mixture was incubated at 56° C. with shaking at 1400 rpm for up to 3 hours. To separate the dissolved fraction (A) from the undissolved fraction (B), the samples were centrifuged and the supernatant (fraction A) was removed from the pellet which contained the undissolved components (fraction B). As described in Example 1, the RNA was isolated from the supernatant (fraction A) and the DNA was isolated from the pellet (fraction B).

Figure 2:
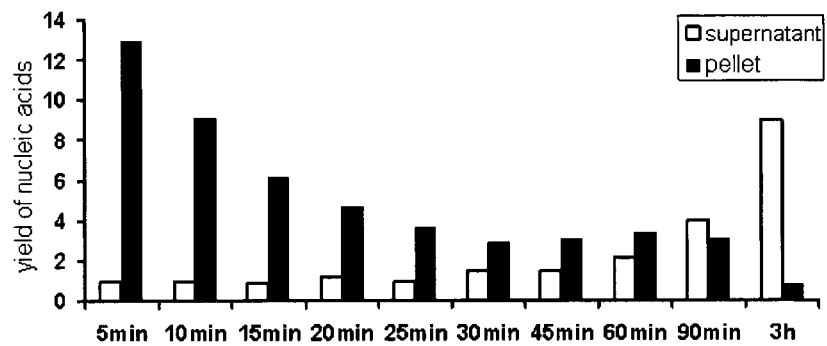
FIG. 2 shows the total yield of the nucleic acids isolated from fraction A (supernatant) and fraction B (pellet) as a function of the reaction time of the proteolytically active compound (Example 3).

To analyze the nucleic acids isolated in this manner, the yield was determined by measuring the absorption at 260 nm. The results are shown in FIG. 2. With increasing reaction time of the proteinase, the yield of nucleic acids decreases in the pellet and increases correspondingly in the supernatant, as more nucleic acids are dissolved from the pellet by the longer proteinase action.

Figure 3:
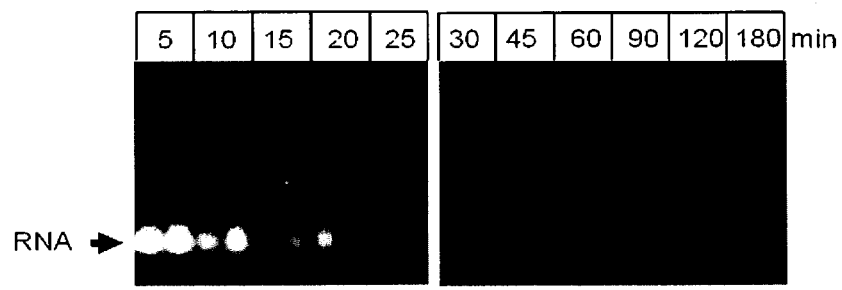
FIG. 3 shows the result of an analysis of the RNA content in fraction B on a TAE-agarose gel as a function of the reaction time of the proteolytically active compound (Example 3).

However, this total distribution of nucleic acids does not provide any information about the DNA and RNA content in the fractions. Therefore, in each case 10 µl of eluate of the DNA-containing fractions (B) were analyzed on a TAE-agarose gel. The result is shown in FIG. 3.

It is clearly evident that after a proteinase K reaction time of only 5 min a large part of the RNA still remains in the undissolved fraction, i.e. the pellet. With increasing proteinase reaction time this amount is reduced, and from a reaction time of 15 min onwards the undissolved fraction comprises only small amounts of RNA, or RNA is substantially no longer detectable. In contrast, the DNA remains considerably longer (for at least 90 min) in the undissolved fraction B. By optimizing the reaction time of the proteolytically active compound, it is thus possible to adjust the distribution of the types of nucleic acid in the two fractions.

Figure 4:
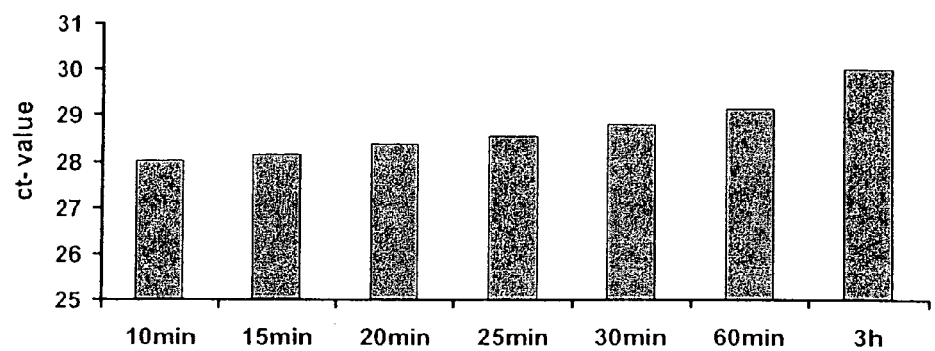
FIG. 4 shows the effect of the reaction time of the proteolytically active compound on the amplification of the DNA obtained from fraction B by quantitative real-time PCR as the change of the ct value (Example 3).

To examine the effect of the length of reaction time of the proteolytically active compound in the process according to the invention, not only on the isolation of the nucleic acids, but also on the analysis by amplification, the DNA was analyzed by quantitative real-time PCR. To this end, in each case identical volumes of the isolated DNA eluates were, in each case in two determinations, used for detecting an amplicon of the prnp gene. Amplification was carried out in a total volume of 25 µl with a mastermix suitable for real-time RT-PCR, such as, for example, the QuantiTect SYBRGreen PCR kit from QIAGEN, according to the manufacturer's instructions. Amplification was carried out in a suitable real-time amplification instrument such as, for example, the ABI PRISM® 7900HT Sequence Detection System from Applied Biosystems (Carlsbad, Calif., USA). The mean values determined from the ct values are shown in FIG. 4.

The results show that with increasing reaction time the ct value increases, which is due to the reduced amount of DNA in the eluate. With increasing reaction time, not only the RNA but also the DNA passes increasingly into the supernatant, where, however, the RNA is dissolved and encountered in the supernatant markedly more rapidly than the DNA. While the gel shows that even after a reaction time of 15 min the RNA is already dissolved virtually completely from the pellet and encountered in the supernatant, the amount of DNA in the undissolved fraction B is, according to gel and real-time PCR, significantly reduced only after more than 90 minutes.

Example 4

Use of Different Aqueous Solutions in the Process According to the Invention

The samples used for this experiment were formalin-fixed and paraffin-embedded tissue samples (FFPE samples) from rat liver which had been stored at room temperature for about 7 months after embedding. With the aid of a microtome, sections of a thickness of about 20 µm were prepared from these samples. In each case, one section per reaction was used. Components of the RNeasy FFPE kit and the QIAamp FFPE kit from QIAGEN were employed for the subsequent isolation of DNA and RNA from the processed samples.

Deparaffinization, rehydration and drying of the sections were carried out as described in Example 2. The deparaffinized sample pellets obtained in this manner were treated with 150 µl of an aqueous solution 1 comprising 20 mM Tris, 2 mM EDTA and 0.2% SDS (pH 7), an aqueous solution 2 comprising 50 mM Tris, 25 mM EDTA, 1% SDS, 0.1% Nonidet NP40 and 500 mM NaCl (pH 7.4) or an aqueous solution 3 comprising 50 mM Tris, 100 mM EDTA, 3% SDS and 10 mM NaCl (pH 8.2) and mixed with 10 µl of a proteinase K solution (>600 mAU/ml) as proteolytically active compound. The mixture was incubated at 56° C. with shaking at 1400 rpm for 15 min. To separate the dissolved fraction (A) from the undissolved fraction (B), the samples were initially cooled on ice for 5 min and then centrifuged at 4° C. The DNA was isolated from the pellet (fraction B) as described in Example 1, the pellet being taken up in a buffer comprising 50 mM Tris, 25 mM EDTA, 1% SDS, 0.1% Nonidet P-40 and 500 mM NaCl (pH 7.4). The yield was determined by measuring the absorption at 260 nm. The results are shown in Table 3.

TABLE 3

| Aqueous solution | Yield of DNA [µg] |
|---|---|
| 1 | 3.0 |
| 2 | 3.7 |
| 3 | 2.3 |

All three aqueous solutions used give a good yield of DNA, certain variations being caused by the heterogeneity of the samples. The example shows that a large number of different aqueous solutions can be used for the process according to the invention, it being possible to vary both the ingredients and their concentration. It is thus possible to adapt the aqueous solution to be used to the proteolytically active compound employed.

Example 5

Isolation of DNA from Different Types of Tissue with the Aid of the Process According to the Invention The samples used were FFPE samples from rat which had been stored at room temperature for different periods of time: kidney (storage time about 13 months), liver (storage time about 6 months), spleen (storage time about 19 months), heart (storage time about 13 months) and lung (storage time about 6 months). With the aid of a microtome, sections of a thickness of about 20 µm were prepared from each of these samples. In each case, one section per reaction was used. Components of the RNeasy FFPE kit and the QIAamp FFPE kit from QIAGEN were employed for the subsequent nucleic acid isolation from the processed samples with the aid of the process according to the invention.

To compare the isolation of DNA with the aid of the process according to the invention with a process established specifically for the purification of DNA from FFPE samples, sections of the same samples were in each case used for DNA isolation with the QIAamp FFPE kit according to the manufacturer's (QIAGEN) instructions and used as control samples.

Deparaffinization, rehydration and drying of the sections were carried out as described in Example 2. The deparaffinized sample pellets obtained in this manner were treated with 150 µl of an aqueous solution comprising 20 mM Tris, 2 mM EDTA and 0.2% SDS (pH 7) and mixed with 10 µl of a proteinase K solution (>600 mAU/ml) as proteolytically active compound. This mixture was incubated at 56° C. with shaking at 1400 rpm for 15 min. To separate the dissolved fraction (A) from the undissolved fraction (B), the samples were initially cooled on ice for 5 min and then centrifuged. The DNA was isolated from the pellet (fraction B) as described in Example 1, with a two-hour incubation at 90° C.

Figure 5:
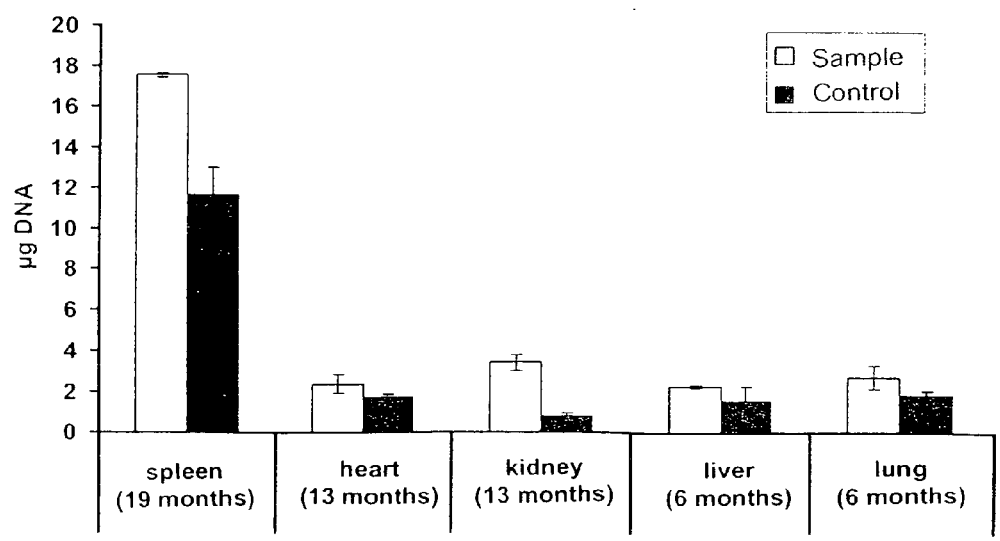
FIG. 5 shows the yield of DNA, determined by UV spectroscopy, which could be isolated using the process according to the invention from various types of tissue stored for the time stated in each case, in comparison to the yield in a process carried out using a commercially available kit (Example 5).

For the analysis of the DNA obtained, the yield was determined by measuring the absorption at 260 nm. The mean values and standard deviations of the duplicate determinations are shown in FIG. 5. With the aid of the process according to the invention, DNA could be isolated from all samples, the yield in all cases exceeding the yield obtained in the control process.

Figure 6:
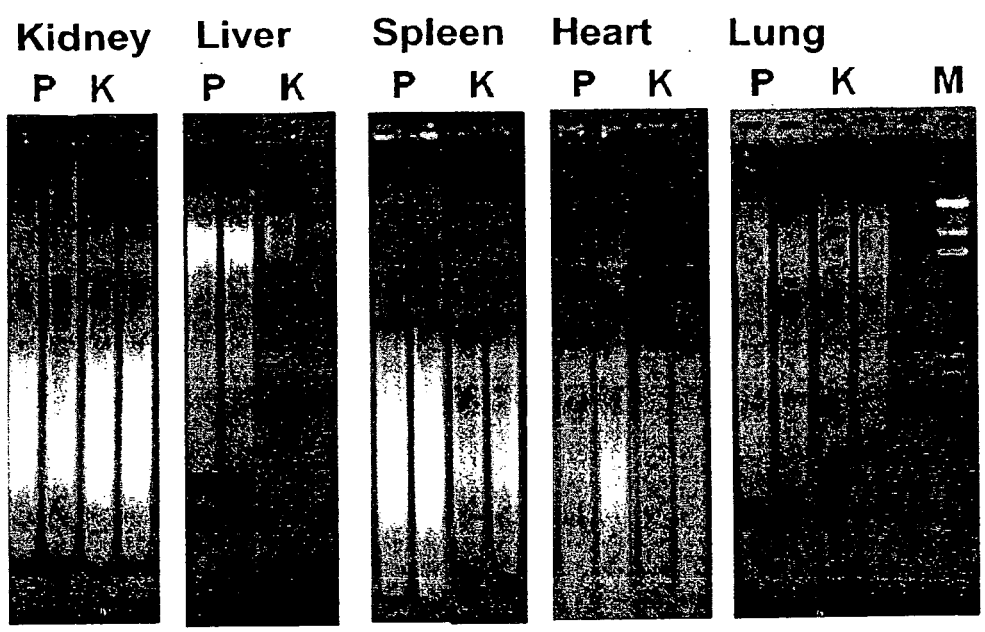
FIG. 6 shows the analysis of the DNA obtained according to Example 5 on a TAE-agarose gel. For size comparison, the size marker Lambda/HindIII (Invitrogen, Carlsbad, Calif., USA) was applied in lane M.

Moreover, in each case 10 µl of the DNA eluate were separated on a TAE-agarose gel and stained with ethidium bromide. The result is shown in FIG. 6. In all cases the DNA isolated with the aid of the process according to the invention showed approximately the same molecular size distribution as the DNA isolated in the control process.

To examine the suitability of the DNA isolated by the process according to the invention for amplification analyses, the DNA obtained in this manner was used in a quantitative real-time PCR assay. Identical volumes of the isolated DNA eluates were used in duplicate determinations for detecting a 465 base pair amplicon of the pmp gene.

In FFPE samples, the DNA is in principle present in fragmented form, the extent of fragmentation and thus the spektrum of the DNA fragments that can be isolated depending inter alia on the nature of the fixation and embedding, but also on the kind of sample and the storage of the sample. Moreover, the extent of crosslinking in the DNA that remains after the isolation of the nucleic acid limits the amplification and in particular the possible size of the amplicon. To ensure efficient amplification in spite of this, preference is in principle given to small amplicons. The amplicon size of 465 bp used here is very big for FFPE samples and was chosen to test the quality and suitability of the DNA isolated by the process according to the invention.

Figure 7:
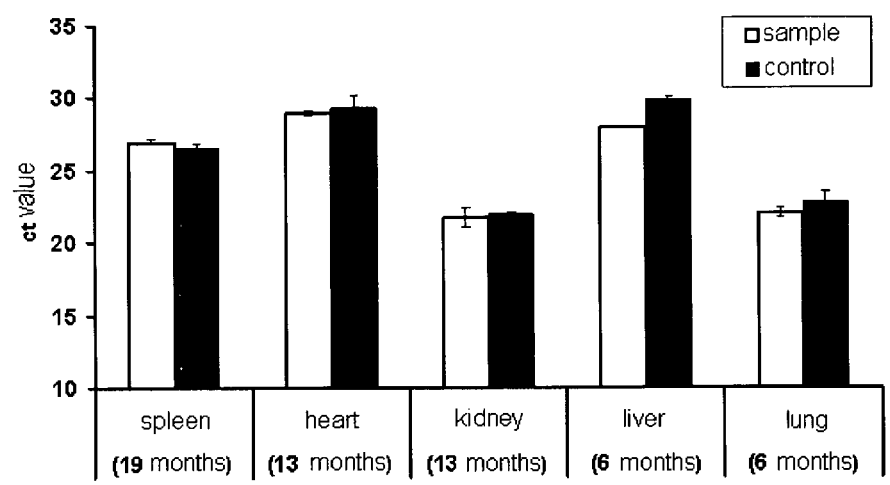
FIG. 7 shows the analysis of the DNA obtained according to Example 5 by real-time PCR analysis.

Amplification was carried out in a total volume of 25 µl with a mastermix suitable for real-time RT-PCR, such as, for example, the QuantiTect SYBRGreen PCR kit from QIAGEN, according to the manufacturer's instructions. Amplification was carried out in a suitable real-time amplification instrument such as, for example, the ABI PRISM® 7900HT Sequence Detection System from Applied Biosystems (Carlsbad, Calif., USA). The measured ct values were used to determine the mean values and standard deviations of the DNA isolated according to the invention, which are shown in FIG. 7.

In all cases, the ct value is comparable to that of the control DNA or even lower, which confirms better amplifiability and/or a higher yield.

In total, the results show that the process according to the invention allows the isolation of DNA from FFPE samples which, with respect to yield, quality, fragment size and suitability for amplification analyses, is at least as good or else better than DNA isolated by a process known from the prior art for the specific isolation of DNA from FFPE samples.

Example 6

Isolation of RNA from Different Types of Tissue by the Process According to the Invention The samples used for this experiment were FFPE samples from rat which had been stored at room temperature for different periods of time: kidney (storage time about 5 months), liver (storage time about 24 months), heart (storage time about 24 months) and lung (storage time about 24 months). With the aid of a microtome, sections of a thickness of about 20 μm were prepared from these samples. In each case, one section per reaction was used. Components of the RNeasy FFPE kit and the QIAamp FFPE kit from QIAGEN were employed for the subsequent nucleic acid isolation from the FFPE sections with aid of the inventive process.

To compare the isolation of RNA with the aid of the process according to the invention with a process established specifically for the purification of RNA from FFPE samples, sections of the same samples were used for the isolation of RNA with the RNeasy FFPE kit according to the manufacturer's (QIAGEN) instructions and used as control samples.

Deparaffinization, rehydration and drying of the sections were carried out as described in Example 2. The deparaffinized sample pellets obtained in this manner were treated with 150 μl of an aqueous solution comprising 20 mM Tris, 2 mM EDTA and 0.2% SDS (pH 7) and mixed with 10 μl of a proteinase K solution (>600 mAU/ml) as proteolytically active compound. This mixture was incubated at 56° C. with shaking at 1400 rpm for 15 min. To separate the dissolved fraction (A) from the undissolved fraction (B), the samples were initially cooled on ice for 5 min and then centrifuged. For further isolation of the RNA, the supernatant (fraction A) was removed and the pellet was discarded.

The supernatant was subsequently incubated at 80° C. for 15 min. The sample was cooled at room temperature for five minutes, after which 20 μl of a conventional DNAse buffer (comprising, for example, 0.46 M Tris-HCl (pH 7.5), 114 mM NaCl, 114 mM $MgCl_2$, 114 mM $CaCl_2$), 15 μl of deionized water and 5 μl of DNAse I solution from QIAGEN were added, and the mixture was incubated at room temperature for 15 min. 400 μl of a chaotropic buffer, for example RLT buffer from QIAGEN, were then added, the mixture was mixed with ethanol, applied to a silica membrane, for example present in the RNeasy MinElute column from QIAGEN, and passed through the membrane by centrifugation at 14 000 rpm for 1 min. The silica membrane was washed twice with 500 μl of the alcohol-containing wash buffer RW2 (QIAGEN). The membrane was dried by 5 minutes of centrifugation at 14 000 rpm, and the RNA was, after a 1-minute incubation, eluted by centrifugation by applying with 30 μl of water.

To analyze the RNA isolated in this manner, the yield was determined by measuring the absorption at 260 nm. The mean values of the duplicate determinations are shown in Table 4.

TABLE 4

| Tissue | Yield [μg] | |
|---|---|---|
| | Sample | Control |
| Lung | 9.1 | 8.2 |
| Liver | 2.7 | 2.6 |
| Kidney | 2.3 | 2.2 |
| Heart | 7.6 | 5.3 |

With the aid of the process according to the invention, it was possible to isolate RNA from all samples, where in all cases the yields obtained with the process according to the invention were comparable to or higher than those of the controls.

To examine the suitability of the RNA isolated by the process according to the invention for amplification analyses, the RNA was used in quantitative real-time RT-PCR assays. Identical volumes of the isolated RNA eluates were used in each case in duplicate determinations for detecting an amplicon of the madH7 transcript and the c-jun transcript. Amplification was carried out in a total volume of 25 μl with a mastermix suitable for real-time RT-PCR, such as, for example, the QuantiTect SYBRGreen RT-PCR kit from QIAGEN, according to the manufacturer's instructions. Amplification was carried out in a suitable real-time amplification instrument such as, for example, the ABI PRISM® 7900HT Sequence Detection System from Applied Biosystems (Carlsbad, Calif., USA). In addition, microRNA16 (miR16) was detected in the RNA eluates using the miScript PCR system, according to the manufacturer's (QIAGEN) instructions by real-time RT-PCR. The mean values obtained from the ct values measured are shown in Table 5.

TABLE 5

| | | Lung (24 months) | Liver (24 months) | Kidney (6 months) | Heart (24 months) |
|---|---|---|---|---|---|
| madH7 | sample | 24.9 | 26.1 | 22.8 | 28.2 |
| | control | 27.6 | 26.8 | 23.6 | 29.2 |
| c-jun | sample | 26.1 | 26.9 | 26.6 | 28.7 |
| | control | 28.2 | 27.2 | 26.7 | 29.7 |
| miR16 | sample | 17.4 | 19.0 | 20.8 | 19.9 |
| | control | 20.44 | 21.1 | 19.4 | 21.2 |

In all cases, the measured ct value of the sample processed according to the invention is comparable to that of the control sample or even lower, which is due to better amplifiability or a larger amount of RNA.

Example 7

DNase Treatment for Efficient miRNA Purification

For this experiment, FFPE samples from rat which had been stored at room temperature for different periods of time were used: brain (storage time about 5 months) and heart (storage time about 18 months). With the aid of a microtome, sections of a thickness of about 20 μm were prepared from these samples. In each case, one section per reaction was used. Components of the RNeasy FFPE kit and the QIAamp FFPE kit from QIAGEN were employed for the subsequent nucleic acid isolation from the FFPE sections with aid of the inventive process.

To compare the isolation of miRNA with the aid of the process according to the invention with a process established specifically for the purification of miRNA from FFPE samples, sections of the same samples were used for the isolation of miRNA with the miRNeasy FFPE kit according to the manufacturer's (QIAGEN) instructions and used as control samples.

The deparaffinized sample pellets obtained in this manner were treated with 150 μl of an aqueous solution comprising 20 mM Tris, 2 mM EDTA and 0.2% SDS (pH 7) and mixed with 10 μl of a proteinase K solution (>600 mAU/ml) as proteolytically active compound. This mixture was incubated at 56° C. with shaking at 1400 rpm for 15 min. To separate the mainly RNA containing dissolved fraction (A) from the mainly DNA containing undissolved fraction (B), the samples were initially cooled on ice for 3 min and then centrifuged. For further isolation of the RNA including miRNA, the supernatant (fraction A) was removed and the DNA containing pellet was discarded.

The supernatant was subsequently incubated at 80° C. for 15 min to reverse the cross-links. The sample was cooled at room temperature for five minutes, after which 20 μl of different buffers for facilitating DNase-activity (pretreatment buffers 1-5, see below), 15 μl water and 5 μl of DNAse I solution from QIAGEN were added. The following buffers were used for this experiment:

pretreatment buffer 1: 0.46 M Tris-HCl (pH 7.5), 114 mM NaCl, 114 mM MgCl$_2$, 114 mM CaCl$_2$ pretreatment buffer 2: 0.46 M Tris-HCl (pH 7.5), 114 mM MgCl$_2$, 114 mM CaCl$_2$ pretreatment buffer 3: 46 mM Tris-HCl (pH 7.5), 11.4 mM NaCl, 11.4 mM MgCl$_2$, 11.4 mM CaCl$_2$ pretreatment buffer 4: 20 mM Tris-HCl (pH 7.5), 100 mM MgCl$_2$, 10 mM CaCl$_2$ pretreatment buffer 5: 20 mM Tris-HCl (pH 7.5), 100 mM MgCl$_2$, 2.5 mM CaCl$_2$ The mixture was incubated at room temperature for 15 min. In order to isolate RNA incl. small RNAs like micro RNAs from the DNase digested sample 400 μl of a chaotropic buffer, for example RLT buffer from QIAGEN, were then added, the mixture was mixed with 1400 μl 96-100% ethanol, applied to a silica membrane, for example present in the RNeasy MinElute column from QIAGEN, and passed through the membrane by centrifugation at 14 000 rpm for 1 min. The silica membrane was washed twice with 500 μl of the alcohol-containing wash buffer RPE (QIAGEN). The membrane was dried by 5 minutes of centrifugation at 14 000 rpm, and the RNA was, after a 1-minute incubation, eluted by centrifugation by applying with 30 μl of water.

For comparison, the same samples were used for purification of RNA incl. small RNAs without DNAse preatreatment but with a common on-column DNAse treatment after binding the RNA onto the membrane. Deparaffinzation and proteinase K digestion were performed as described above. After that, 320 μl of a chaotropic buffer, for example RLT buffer from QIAGEN, were then added, the mixture was mixed with 1120 μl 96-100% ethanol, applied to a silica membrane, for example present in the RNeasy MinElute column from QIAGEN, and passed through the membrane by centrifugation at 14 000 rpm for 1 min. The silica membrane was washed with 350 μl of a wash buffer containing chaotropic reagents and ethanol, like buffer RWT (QIAGEN). 80 μl of a mixture comprising 10 μl DNase 1 and an appropriate DNAse buffer (e.g. buffer RDD (QIAGEN)) was applied then onto the membrane and incubated for 15 min at room temperature. After that the membrane was again washed with buffer RWT and washed twice with 500 μl of the alcohol-containing wash buffer RPE (QIAGEN). The membrane was dried by 5 minutes of centrifugation at 14 000 rpm, and the RNA was, after an 1-minute incubation, eluted by centrifugation by applying with 30 μl of water.

Figure 8:
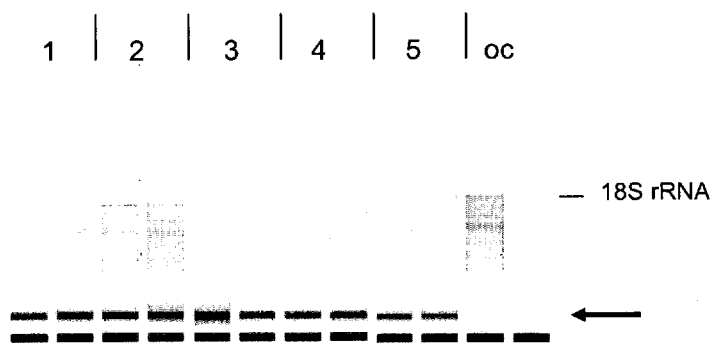
FIG. 8 shows an Agilent Bioanalyzer analysis of isolated RNA. 1-5: Samples with DNAse pretreatment using pretreatment buffer 1-5 described in example 1. oc: Samples without DNAse pretreatment, but with on column DNAse treatment as it is common in the prior art.

To analyze the RNA isolated in this manner, exemplary the RNA from brain was analyzed using an Agilent Bioanalyzer, which separates the RNA molecules depending on size. FIG. 8 shows the results of Bioanalyzer measurement. RNA from FFPE samples is always partly degraded and the extent of degradation is dependent on multiple factors like fixation, embedding and storage of the sample and the RNA extraction method. Therefore, the gel-like visualization of the RNA shows in all cases partly degraded RNA (see FIG. 8). The 28S rRNA is not and the 18S rRNA is only weekly visible. In addition, a lot of RNA fragments occur from the size of the 28srRNA band down to low molecular weights. The common on column DNAse treatment results in very low yields of the smallest RNA population in miRNA (see arrow). In contrast, DNAse pretreatment prior to column loading according to the present invention allows isolation of high amounts of the very low molecular weight RNAs.

In order to determine efficiency of miRNA purification in particular, the purified RNA was analyzed for detection and quantitation of miRNA 16 using the miScript PCR System, according to the manufacturer's (QIAGEN) instructions by real-time RT-PCR. The mean values obtained from the ct values measured are shown in Table 1.

TABLE 6

| DNAse treatment | Brain | heart |
|---|---|---|
| pretreatment buffer 1 | 18.30 | 20.03 |
| pretreatment buffer 2 | 18.17 | 19.39 |
| pretreatment buffer 3 | 18.17 | 20.43 |
| pretreatment buffer 4 | 18.25 | 20.06 |
| pretreatment buffer 5 | 18.63 | 19.91 |
| On-column DNase treatment | 20.33 | 21.49 |

In all cases, the ct values measured are lower in samples with DNAse pretreatment, whereas on-column DNAse treatment gives significant higher ct values. Lower ct values represent higher amounts of miRNA with a ct value difference of one indicating of about the double amount of detected miRNA. Thus, DNAse pretreatment before isolating the RNA significantly enhances miRNA purification efficiency over the on-column DNase digest according to the state of art.

Overall, the results show that the process according to the invention allows the isolation of RNA from FFPE samples which, with respect to yield, quality, fragment size and suitability for amplification analyses, is at least as good as RNA isolated by an isolation process known from the prior art and specific for the isolation of RNA from FFPE samples.

The invention claimed is:

1. A process for obtaining ribonucleic acids (RNA) in a dissolved liquid fraction and deoxyribonucleic acids (DNA) in an undissolved solid fraction from a single biological sample fixed by cross-linking, comprising:
   a) partially dissolving the sample in an aqueous buffer solution with simultaneous partial proteolysis of the protein-containing components of the sample using at least one proteolytically active compound, thereby obtaining a mixture that comprises a dissolved liquid fraction and an undissolved solid fraction, wherein the dissolved liquid fraction comprises mainly RNA based on the total amount of nucleic acids in the dissolved liquid fraction, and wherein the undissolved solid fraction comprises mainly DNA based on the total amount of nucleic acids in the undissolved solid fraction; and
   b) separating the dissolved liquid fraction of step (a) from the undissolved solid fraction of step (a), wherein step (b) is not performed by adding to the mixture of step (a) an organnic solvent or a solid matrix that selectively bind one or both types of nucleic acid.

2. The process of claim 1, further comprising, after step b), isolating RNA from the dissolved liquid fraction, and/or isolating DNA from the undissolved solid fraction.

3. The process of claim 1, wherein the aqueous buffer solution comprises at least one buffer substance.

4. The process of claim 3, wherein the at least one buffer substance is selected from the group consisting of Tris, Hepes, Pipes, Mops and alkali metal acetate/acetic acid.

5. The process of claim 3, wherein the aqueous buffer solution further comprises at least one surfactant.

6. The process of claim 5, wherein the at least one surfactant is selected from the group consisting of sodium dodecylsulphate (SDS), sodium deoxycholate, 3-(3-cholamidopropyl)dimethylammonim-1-propanesulphonate (CHAPS), polyethylene glycol phenyl ethers, and mixtures thereof.

7. The process of claim 5, wherein the at least one surfactant is sodium dodecylsulphate, polyethylene glycol nonylphenyl ether having a degree of ethoxylation of 40, and/or polyethylene glycol (1,1,3,3-tetramethylbutyl)phenyl ether having a degree of ethoxylation of 9-10.

8. The process of claim 3, wherein the aqueous buffer solution further comprises at least one substance selected from the group consisting of complex formers, chaotropic agents, reducing agents, and inorganic salts.

9. The process of claim 8, wherein the complex former is ethylenediamine-N,N,N',N'-tetraacetic acid (EDTA), ethylene glycol bis(2-aminoethyl ether)-N,N,N',N'-tetraacetic acid (EGTA) sodium citrate, or a mixture of EDTA and EGTA.

10. The process of claim 8, wherein the chaotropic agent is selected from the group consisting of guanidine hydrochloride, guanidine thiocyanate, guanidine isothiocyanate, perchlorates, NaI, KI, and urea.

11. The process of claim 10, wherein the chaotropic agent is in a concentration from 0.1 to 10 M.

12. The process of claim 8, wherein the reducing agent is selected from the group consisting of dithiothreitol (DTT), dithioerythritol (DTE), sodium thiosulfate, β-mercaptoethanol, and mixtures thereof.

13. The process of claim 8, wherein the inorganic salt is an alkali metal halide, an ammonium salt, a lithium sulphate, or a mixture thereof.

14. The process of claim 13, wherein the alkali metal halide is NaCl, KCl or LiCl, or an alkaline earth metal halide.

15. The process of claim 14, wherein the alkaline earth metal halide is $CaCl_2$ or $MgCl_2$.

16. The process of claim 13, wherein the ammonium salt is ammonium chloride or ammonium sulphate.

17. The process of claim 8, wherein the aqueous buffer solution has a pH in the range from 6 to 9.

18. The process of claim 17, wherein the aqueous buffer solution has a pH in the range from 6.5 to 8.5.

19. The process of claim 18, wherein the aqueous buffer solution has a pH in the range from 6.8 to 7.5.

20. The process of claim 1, wherein the proteolytically active compound is selected from the group consisting of proteases and non-enzymatic proteolytically active compounds.

21. The process of claim 20, wherein the proteolytically active compound is selected from the group consisting of proteinase K, trypsin, chymotrypsin, papain, pepsin, pronase, endoproteinase Lys-C and cyanogen bromide, and mixtures thereof.

22. The process of claim 20, wherein the proteolytically active compound comprises proteinase K.

23. The process of claim 20, wherein the total concentration of the proteolytically active compounds in the aqueous solution is in a range of from 0.001 to 5% by weight based on the total weight of the aqueous solution.

24. The process of claim 23, wherein the total concentration of the proteolytically active compounds in the aqueous solution is in a range of from 0.01 to 2.5% by weight based on the total weight of the aqueous solution.

25. The process of claim 23, wherein the total concentration of the proteolytically active compounds in the aqueous solution is in a range of from 0.05 to 0.2% by weight based on the total weight of the aqueous solution.

26. The process of claim 1, wherein step a) takes place by incubating the sample in the aqueous buffer solution.

27. The process of claim 26, wherein step a) takes place by incubating the sample in the aqueous buffer solution at a temperature from 18 to 80° C.

28. The process of claim 26, wherein step a) takes place by incubation of the sample in the aqueous buffer solution at a temperature from 50 to 65° C.

29. The process of claim 26, wherein the sample is incubated in the aqueous buffer solution for a period of from 30 seconds to 5 days.

30. The process of claim 29, wherein the sample is incubated in the aqueous buffer solution for a period of from 1 minute to 5 hours.

31. The process of claim 30, wherein the sample is incubated in the aqueous buffer solution for a period of from 5 to 90 minutes.

32. The process of claim 31, wherein the sample is incubated in the aqueous buffer solution for a period of from 10 to 30 minutes.

33. The process of claim 1, wherein the biological sample fixed by cross-linking is a paraffin-embedded sample.

34. The process of claim 33, wherein the paraffin-embedded sample is a formalin-fixed paraffin-embedded sample.

35. The process of claim 33, further comprising, prior to step a), step (i) for the selective removal of the paraffin.

36. The process of claim 35, wherein step (i) comprises bringing the sample into contact with a hydrophobic organic solvent, optionally with addition of a $C_1$-$C_5$-alcohol.

37. The process of claim 36, wherein the hydrophobic organic solvent comprises an apolar aliphatic or aromatic hydrocarbon of a chain length of more than 6 and less than 17 carbon atoms or a mixture thereof.

38. The process of claim 36, wherein step i) is performed by bringing the sample into contact with a hydrocarbon or hydrocarbon mixture selected from the group consisting of xylene, heptane and mineral oil, optionally with addition of 1-25% by volume of methanol or ethanol.

39. The process of claim 35, further comprising, after step (i) and before step a), one or more of the following steps:
  (ii) rehydration of the sample,
  (iii) drying of the sample, and
  (iv) homogenization of the sample.

40. The process of claim 39, wherein step (ii) is performed by repeated washing of the sample with aqueous $C_1$- to $C_5$-alcohol solutions of successively increasing water content.

41. The process of claim 1, further comprising subjecting the undissolved solid fraction to lysis with simultaneous enzymatic protease digestion to release the DNA from the undissolved solid fraction.

42. The process of claim 1, further comprising isolating RNA from the dissolved liquid fraction, and/or isolating DNA from the undissolved solid fraction, wherein the isolation of RNA and/or DNA is performed by precipitation, binding to nucleic acid-binding materials, electrophoresis, and/or chromatography.

43. The process according claim 1, wherein the undissolved solid fraction is discarded after separation.

44. The process of claim 1, further comprising performing a DNase digest on the dissolved liquid fraction, and subsequently isolating the RNA from said fraction.

45. The process of claim 1, further comprising isolating or purifying RNA from the dissolved liquid fraction and/or DNA from the undissolved solid fraction, and detecting the isolated and/or purified RNA and/or DNA.

46. The process of claim 45, wherein detecting the isolated and/or purified RNA and/or DNA is performed by a technique selected from the group consisting of amplification techniques, gel electrophoresis, blotting techniques, microarray analyses, restriction fragment length polymorphism analyses (RFLP analyses), SAGE (serial analysis of gene expression), sequencing, single nucleotide polymorphism analyses (SNP analyses), mutation analyses, epigenetic analyses, and combinations thereof.

47. The process of claim 46, wherein the amplification technique is PCR, qPCR, RT-PCR, qRT-PCR, or whole genome amplification.

48. The process of claim 46, wherein the blotting technique is Southern blotting or Northern blotting.

49. The process of claim 46, wherein the sequencing is Next Generation sequencing or RNA sequencing.

50. The process of claim 46, wherein the epigenetic analysis is an analysis of methylation patterns.

51. The process of claim 1, further comprising isolating RNA from the dissolved liquid fraction and/or DNA from the undissolved solid fraction, wherein the isolated RNA and/or DNA is used for analyzing and/or quantification of the RNA and/or DNA.

52. The process of claim 1, further comprising isolating RNA from the dissolved liquid fraction and/or DNA from the undissolved solid fraction, wherein the isolated RNA and/or DNA is used for diagnosis, prognosis, decisions with respect to a therapy, and/or monitoring a therapy, of a disease.

53. The process of claim 1, wherein step (b) is performed by centrifugation.

54. The process of claim 1, wherein step (b) is performed by filtration, sedimentation, or decantation.

55. The process of claim 1, further comprising isolating or purifying RNA from the dissolved liquid fraction and isolating DNA from the undissolved solid fraction so that RNA and DNA are isolated or purified in parallel from the single biological sample.

\* \* \* \* \*